United States Patent [19]

Hellerstein

[11] Patent Number: 5,338,686
[45] Date of Patent: Aug. 16, 1994

[54] METHOD FOR MEASURING IN VIVO SYNTHESIS OF BIOPOLYMERS

[76] Inventor: Marc K. Hellerstein, 4 Anson Way, Kensington, Calif. 94707

[21] Appl. No.: 876,752

[22] Filed: Apr. 29, 1992

[51] Int. Cl.[5] .................. G01N 31/00; G01N 24/00; G01N 33/543
[52] U.S. Cl. .................................. 436/173; 424/9; 436/174; 436/177
[58] Field of Search ............ 436/174, 173, 177, 518, 436/501, 542; 534/551; 424/9

[56] References Cited

U.S. PATENT DOCUMENTS

| | | | |
|---|---|---|---|
| Re. 33,524 | 1/1991 | Schram | 436/177 |
| 3,959,287 | 5/1976 | Goldstein et al. | 436/173 |
| 4,022,876 | 5/1977 | Anbar | 436/542 |
| 4,224,031 | 9/1980 | Mee et al. | 436/173 |
| 4,732,864 | 3/1988 | Tolman | 436/173 |
| 4,866,270 | 9/1989 | Hall et al. | 436/173 |
| 4,952,685 | 8/1990 | Stavrianopoulos | 534/551 |
| 4,957,858 | 9/1990 | Chu et al. | 436/501 |
| 4,970,144 | 11/1990 | Fareed et al. | 436/518 |
| 5,059,415 | 10/1991 | Neuwelt | 436/173 |
| 5,084,266 | 1/1992 | McKenzie et al. | 436/173 |
| 5,124,267 | 6/1992 | Humpel et al. | 436/173 |

OTHER PUBLICATIONS

Inbar et al. "$^{13}$C-NMR and GC-MS Studies of carbon metabolism in the Actinomycin D producer *Streptomyces parvolus* by Use of $^{13}$C-labeled precursors"; J. Bact.; vol. 173, No. 24, Dec. 1991, pp. 7790–7801.

Inbar et al. "$^{13}$C-NMR, $^{1}$H-NMR and GC-MS studies of the biosynthesis of (1987) $^{13}$C-enriched L-lysine by *Brevibacterium flavum*"; Eur. J. Biochem. vol. 162, No. 3, 621–633.

Kalderon et al. "Glucose recycling and production in glycogenosis type I and III stable isotope technique study"; Ame. J. Phys.; vol. 257, No. 3, pt 1. pp. E346–E353, Sep. 1989.

Des Rosiers et al. "Interpretation of isotopomer patterns in tracing glycogen, synthesis and glucose recycling using $^{13}$C$_{6}$]glucose," Ame. J. Phys. v. 259 No. 5, pp. E757–E762, (Nov. 1990).

Matucha et al. "Isotope effect in gas-liquid chrom. of labeled compounds", J. Chrom. vol. 588 Nos. 1&2, pp. 251–258, Dec. 27, 1991.

Katz et al. "Application of Mass isotopomer analysis for det. of pathways of glycogen synthesis"; Ame. J. Phys.; vol. 261, No. 3, pt. 1 pp. E332–E336.

Hellerstein, M. K., et al., "Measurement of De Novo Hepatic Lipogenesis in Humans Using Stable Isotopes," J. Clin. Invest. 87:1841–1852 (1991).

Hellerstein, M. K., "Relationship Between Precursor Enrichment and Ratio of Excess $M_2$/Excess $M_1$ Isotopomer Frequencies in a Secreted Polymer," J. Biol. Chem. 266(17):10920–10924 (1991).

Hellerstein, M. K., et al., "Sampling the Lipogenic Hepatic Acetyl-CoA Pool in Vivo in the Rat: Comparison of Xenobiotic Probe to Values Predicted from Isotopomeric Distribution in Circulating Lipids and (List continued on next page.)

*Primary Examiner*—Robert J. Warden
*Assistant Examiner*—Ramon Torres
*Attorney, Agent, or Firm*—Carol A. Stratford; Peter J. Dehlinger

[57] ABSTRACT

A method for determining the mass isotope enrichment of a subunit from which a biopolymer is formed, and the rates of synthesis and decay of the biopolymer. The mass isotope enrichment of the subunit is determined by comparing the mass isotopomer distribution of the biopolymer after administration of a mass isotopically labeled subunit, with the expected frequencies of the different mass isotopomers produced from a given subunit mass isotope enrichment. To determine the synthesis rate of the biopolymer, the expected frequency of a selected biopolymer mass isotopomer, calculated from the subunit isotope enrichment, is compared with the actual frequency of that biopolymer mass isotopomer. To determine biopolymer decay, the decay rate of high mass isotopomers of the biopolymer is determined.

9 Claims, 9 Drawing Sheets

OTHER PUBLICATIONS

Measurement of Lipogenesis and Acetyl–CoA Dilution," J. Biol. Chem. 266(17):10912–10919 (1991).

Hellerstein, M. K., et al., "Use of mass isotopomer distributions in secreted lipids to sample lipogenic acetyl–CoA pool in vivo in humans," Am. J. Physiol. 261:E479–E486 (1991).

Katz, J., et al., "Studies of Glycogen Synthesis and the Krebs Cycle by Mass Isotopomer Analysis with [U–$^{13}$C]Glucose in Rats," J. Bio. Chem. 264(22):12994–13001 (1989).

Kelleher, J. K., and Masterson, T. M., "Model equations for condensation biosynthesis using stable isotopes and radioisotopes," Am. J. Physiol. 262:E118–E125 (1992).

Lapidot, A., "Inherited Disorders of Carbohydrate Metabolism in Children Studied by $^{13}$C–Labelled Precursors, NMR and GC–MS," J. Inher. Metab. Dis. 13:466–475 (1990).

Lee, W.–N. P., "Analysis of Mass Isotopomer Data," J. Biol. Chem. 264(22):13002–13004 (1989).

Lee, W.–N. P., et al., "Mass Isotopomer Pattern and Precursor–Product Relationship," Biological Mass Spectrometry 21:114–122 (1992).

Fig. 1A

FOR MEASURING BIOSYNTHESIS:

ADMINISTER TRACER, COLLECT BLOOD OR TISSUE
↓
PURIFY POLYMER AND ANALYZE ION CLUSTER BY MS

|  | $M_1/M_{0-4}$ | $M_2/M_{0-4}$ | $M_3/M_{0-4}$ | $M_4/M_{0-4}$ |
|---|---|---|---|---|
| BSLN | 0.2284 | 0.0363 | 0.0044 | 0.0012 |
| $t_1$ | 0.2339 | 0.0424 | 0.0068 | 0.0019 |
| $t_2$ | 0.2343 | 0.0424 | 0.0069 | 0.0019 |

↓
CALCULATE MOLAR EXCESSES

|  | $EM_1$ | $EM_2$ | $EM_3$ | $EM_4$ |
|---|---|---|---|---|
| $t_1$ | 0.0055 | 0.0061 | 0.0024 | 0.0007 |
| $t_2$ | 0.0060 | 0.0061 | 0.0025 | 0.0007 |

↓
DETERMINE RATIOS (R) AMONG EXCESSES

|  | $EM_1/\Sigma EM_{1-4}$ | $EM_2/\Sigma EM_{1-4}$ | $EM_3/\Sigma EM_{1-4}$ | $EM_3/\Sigma EM_{1-4}$ |
|---|---|---|---|---|
| $t_1$ | 0.3746 | 0.4151 | 0.1635 | 0.0468 |
| $t_2$ | 0.3910 | 0.4008 | 0.1629 | 0.0453 |

↓
CALCULATE P FROM R'S, USING REGRESSION EQUATIONS

|  | $P(EM_1)$ | $P(EM_2)$ | $P(EM_3)$ | $P(EM_4)$ |
|---|---|---|---|---|
| $t_1$ | 0.0535 | 0.0522 | 0.0535 | 0.0586 |
| $t_2$ | 0.0506 | 0.0426 | 0.0533 | 0.0574 |

↓
CALCULATE A* FROM P'S, USING REGRESSION EQUATIONS

|  | $P[(EM_1+EM_3)/2]$ | $A^*(EM_1)$ |
|---|---|---|
| $t_1$ | 0.0535 | 0.1543 |
| $t_2$ | 0.0520 | 0.1548 |

↓
COMPARE ACTUAL MOLAR EXCESSES IN POLYMER TO CALCULATED A*'S TO DETERMINE f

|  | $EM_1$ | $A^*(EM_1)$ | f(%) |
|---|---|---|---|
| $t_1$ | 0.0055 | 0.1543 | 3.59 |
| $t_2$ | 0.0060 | 0.1548 | 3.85 |

↓
COMPARE PER CARBON ENRICHMENT TO P, TO DETERMINE f

|  | $EM_1$ | A.P.E. | f(%) |
|---|---|---|---|
| $t_1$ | 0.0535 | 0.00185 | 3.46 |
| $t_2$ | 0.0520 | 0.00189 | 3.63 |

FOR MEASURING ISOTOPIC DECAY (TURNOVER, DILUTION):

DISCONTINUE TRACER ADMINISTRATION; COLLECT BLOOD OR TISSUE OVER TIME

↓

PURIFY POLYMER AND ANALYZE BY MS; CALCULATE MOLAR EXCESSES

|  | $EM_1$ | $EM_2$ | $EM_3$ | $EM_4$ |
|---|---|---|---|---|
| $t_1$ | 0.0053 | 0.0048 | 0.0019 | 0.0006 |
| $t_2$ | 0.0045 | 0.0042 | 0.0014 | 0.0004 |
| $t_3$ | 0.0029 | 0.0032 | 0.0011 | 0.0003 |
| $t_4$ | 0.0030 | 0.0025 | 0.0009 | 0.0003 |

↓

DETERMINE RATIOS (R) (PARTICULARLY FOR HIGHER MASSES)

|  | $R$ $(EM_2)$ | $R$ $(EM_3)$ | $R$ $(EM_4)$ |
|---|---|---|---|
| $t_4$ | 0.3785 | 0.1539 | 0.0441 |
| $t_5$ | 0.4002 | 0.1303 | 0.0393 |
| $t_6$ | 0.4198 | 0.1473 | 0.0463 |
| $t_7$ | 0.3711 | 0.1343 | 0.0523 |

↓

SELECT TIME POINTS AND MASSES FOR WHICH R IS STABLE, TO CALCULATE DECAY CONSTANT (k)

|  | $\sum_{i=2}^{4} M_i N_i$ | $\sum_{i=3}^{4} M_i N_i$ | $k(hr^{-1})$ |
|---|---|---|---|
| $t_4$ | 0.0175 | 0.0080 | : |
| $t_5$ | 0.0142 | 0.0058 | : |
| $t_6$ | 0.0111 | 0.0047 | : |
| $t_7$ | 0.0091 | 0.0041 | : |

Fig. 1B

| SUBJECT | TIME | 271/270 | 272/270 | EM1(C16) | EM2(C16) | EM2/EM1 | P(C16) | C16 EM1 (A*) | EF (M1/M0-2) | %DeNovo C16 |
|---|---|---|---|---|---|---|---|---|---|---|
| MF2 | BSLN | 0.1999 | 0.0221 | | | | | | | |
| | D1 800 | 0.2302 | 0.0308 | 0.0190 | 0.0063 | 0.3342 | 0.0293 | 0.1478 | | 12.8301 |
| | 900 | 0.2334 | 0.0314 | 0.0210 | 0.0067 | 0.3218 | 0.0272 | 0.1388 | | 15.0985 |
| | 1300 | 0.2476 | 0.0344 | 0.0296 | 0.0087 | 0.2960 | 0.0227 | 0.1196 | | 24.7052 |
| | 1500 | 0.2522 | 0.0356 | 0.0323 | 0.0096 | 0.2964 | 0.0228 | 0.1199 | | 26.9059 |
| | 1700 | 0.257 | 0.0368 | 0.0351 | 0.0104 | 0.2955 | 0.0226 | 0.1192 | | 29.4073 |
| | 1800 | 0.2532 | 0.0357 | 0.0329 | 0.0096 | 0.2925 | 0.0221 | 0.1170 | | 28.0952 |
| | 2000 | 0.2389 | 0.0321 | 0.0244 | 0.0072 | 0.2941 | 0.0224 | 0.1182 | | 20.6253 |
| | 2200 | 0.2269 | 0.0291 | 0.0171 | 0.0051 | 0.2978 | 0.0230 | 0.1210 | | 14.1082 |
| | 2400 | 0.2222 | 0.0274 | 0.0142 | 0.0038 | 0.2699 | 0.0182 | 0.0997 | | 14.2819 |
| | D2 | 0.2127 | 0.0254 | 0.0082 | 0.0024 | 0.2960 | 0.0227 | 0.1196 | | 6.8674 |

Fig. 6

METHOD FOR MEASURING IN VIVO SYNTHESIS OF BIOPOLYMERS

1. FIELD OF THE INVENTION

The present invention relates to methods for measuring the synthesis in vivo of biopolymers from exogenously added isotopically labeled biopolymer subunit precursors and for measuring the contribution to the precursor biopolymer subunit pool of such exogenously added biopolymer subunit precursors. In addition, the present invention relates to a method for estimating the turnover or flux of such synthesized biomolecules, based on isotopic decay in the biomolecules.

2. REFERENCES

Ballard, F.J. (1972) Am. J. Clin. Nutr. 25: 773–779.

Biemann, K., (1990) in *Mass Spectrometry of Biological Materials* (McEwen, C., ed.) 3–21, Marcel Dekker, NY.

Christie, W.W. (ed.) (1982) *Lipid Analysis*, 2nd Ed., 52–53, Pergammon Press, NY.

Deines, P., ( 1980 ) "The isotopic composition of reduced organic carbon" in *Handbook of Environmental Isotope Geochemistry,* (Fritz, P., e t al., eds. ) Vo 1. I, Ch. 9, Elsevier Press, Amsterdam, The Netherlands.

Dietschy, J.M., et al., (1974) J. Biol. Chem. 249..: 52–58.

Foster, D.W., et al., ( 1963 ) J. Biol. Chem. 238:888–892.

Hellerstein, M.K., et al., (1991a) J. Biol. Chem. 266: 10912–10919.

Hellerstein, M.K., et al., (1991b) Am. J. Physiol. 261: E479–E486.

Hellerstein, M.K., (1991c) J. Biol. Chem. 266: 0920–10924.

Hellerstein, M.K., (1991d) J. Clin. Invest. 87 1841–1852.

Jungas, R.L., (1968) Biochemistry ! : 3708–3717.

Knowles, S. E., et al., (1974) Biochem. J. 142: 401–411.

Reid, J.S., et al. , ( 1990 ) Biomed. Mass Spectrom. 19:535–540.

Scofield, R.F., et al., ( 1983 ) Metabolism 32: 1009–1012.

Von Schacky, C., et al., (1985) J. Clin. Invest. 76: 1626–1631.

Waterlow, J.C., et al., eds., (1978) *Protein Turnover in mammalian tissues and in the Whole Body,* North-Holland Publishing Co., Amsterdam, The Netherlands.

Williamson, D., et al., (1974) in *Methods in Enzymatic Analysis* (Bergmeyer, H., ed.) 4: 1836–1837, Academic Press Inc., NY.

Wolfe, R.R., (1984) *Radio-Isotope and Stable Isotope/Mass Spectrometric Methods,* Alan R. Liss, Inc., NY.

Zavaroni, I., et al., (1982) Metabolism 31:1077–1083.

3. BACKGROUND OF THE INVENTION

In order to measure the biosynthesis of a macromolecule or biopolymer composed of subunits, it is necessary to know the degree of labeling (specific activity or enrichment) of its biosynthetic precursor units. In simplest terms, the turnover rate of a biosynthetic product is determined by the rate at which its specific activity or enrichment approaches the specific activity or enrichment of its precursor. Mathmatically, this represents the asymptotic value toward which the product approaches (Waterlow).

Similarly, the fraction of a product derived from a precursor is calculated from the ratio of their specific activities or enrichments (Wolfe). The experimental inaccessibility of intracellular precursors coupled with the complexity of subcellular biochemical organization and the existence of discrete pools of precursors complicates investigation of the turnover of macromolecules, including proteins, lipids, nucleic acids and carbohydrates.

The essence of the problem is that the functional ("true") precursor for a macromolecule may come from a special subcellular pool which may not be readily isolated using biochemical fractionation techniques. An experimental solution to this problem would be to measure the true precursor specific activity or enrichment for each product molecule without having to isolate biochemically the actual intracellular precursor molecule involved. True endogenous synthesis of the product could then be determined.

4. SUMMARY OF THE INVENTION

The invention includes, in one aspect, a method for determining the proportion of mass isotopomers of a subunit in a subunit pool from which a biopolymer containing at least two such subunits is synthesized in a subject. The method includes administering to the subject, such a subunit which is mass isotopically labeled, thereby producing after a selected period of subunit incorporation, an enrichment of the mass isotopically labeled subunit in the biopolymer.

The biopolymer is isolated from the subject after such incorporation period, and using mass spectrometry, the relative frequencies of at least two different mass isotopomers of the biopolymer which each contain at least one mass isotopically labeled subunit is determined. These relative frequencies are used to calculate the proportion of mass isotopically labeled subunit in the subunit pool from which the biopolymer was synthesized.

In a preferred embodiment, the proportion of mass, isotopically labeled subunit in the subunit pool is calculated by comparing the relative frequencies of the different mass isotopomers of the biopolymer with the statistically expected frequencies of mass isopically labeled subunits in a biopolymer formed from a pool containing different ratios of unlabeled and mass isotopically labeled subunits.

Also in a preferred embodiment, determining the relative frequencies of the different mass isotopomers of the biopolymer includes correcting the relative frequencies of said different mass isotopomers of the biopolymer for the relative frequencies of the biopolymers prior to administering the mass isotopically labeled subunit.

In another aspect, the invention includes a method for measuring the rate of synthesis of a biopolymer which is formed from a subunit contained in a subunit pool in a subject. The method applies the steps above to determine the proportion of mass isotopomers of a subunit in a subunit pool from which a biopolymer containing at least two such subunits is synthesized in a subject. From this is calculated the expected frequency of a biopolymer containing at least one mass isotopically labeled subunit. The expected frequency of this biopolymer is compared with the actual determined frequency, to determine the proportion of biopolymer which is newly synthesized during the selected incorporation period.

Also included in the invention is a method for measuring the rate of in vivo decay of a biopolymer which is formed from a subunit contained in a subunit pool in a subject. The method includes administering to a subject, such a subunit which is mass isotopically labeled, producing after a selected period of subunit incorporation, a mass isotopomer of a biopolymer which is produced in negligible amounts only, prior to and after cessation of said administering. The biopolymer is isolated from the subject at least two different times after the mass isotopically labeled subunit is administered. Using mass spectrometry, the frequencies of said mass isotopomer of the biopolymer at the different time points are determined, and from this, the rate of decay of the biopolymer can be calculated.

These and other objects and features of the invention will become more fully apparent when the following detailed description of the invention is read in conjunction with the accompanying drawings.

BRIEF DESCRIPTION OF THE DRAWINGS

FIG. 1 shows a flow diagram of the steps used in carrying out the various methods of the invention, including estimation of proportion of mass isotopomers in the subunit precursor pool and biosynthetic rates (1A) and measurement of isotopic decay for estimation of turnover rate (1B);

FIG. 6 shows palmitate isotopomer ratios from an obese male subject.

DETAILED DESCRIPTION OF THE INVENTION

I. Definitions

Figure 2A:
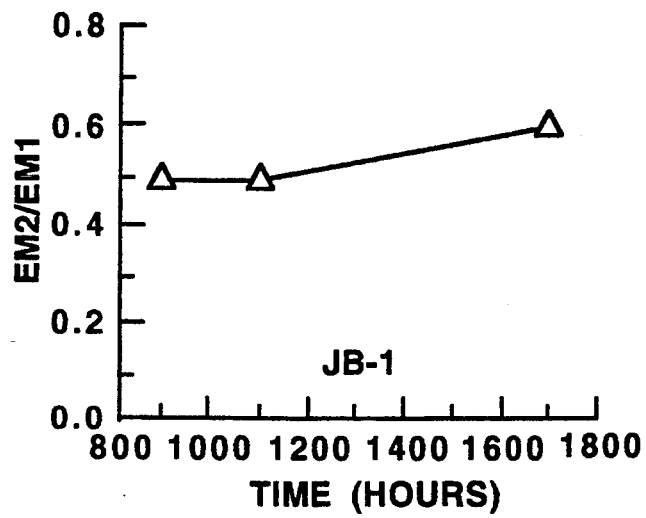
FIG. 2(a–h) shows plots of the ratios $EM_2/EM_1$ isotopomer frequencies over time during infusions of $[1-^{13}C]$- or $[2-^{13}C]$acetate in several subjects.
Figure 2B:
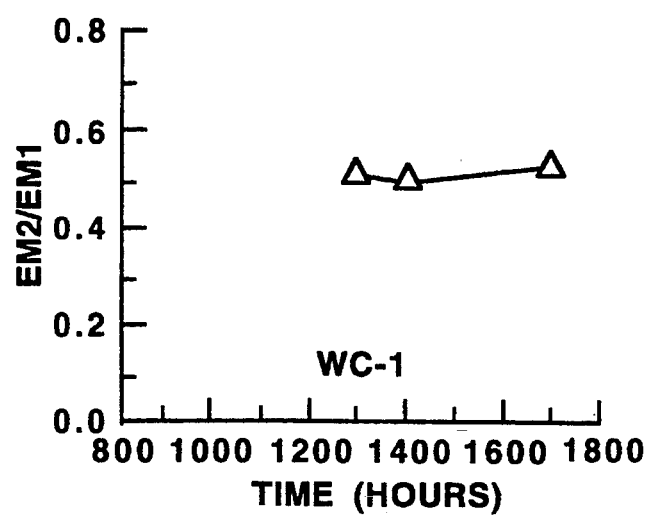
Figure 2C:
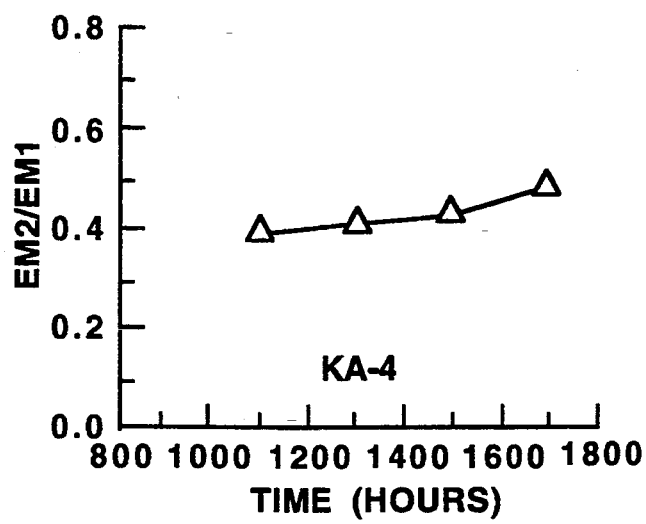
Figure 2D:
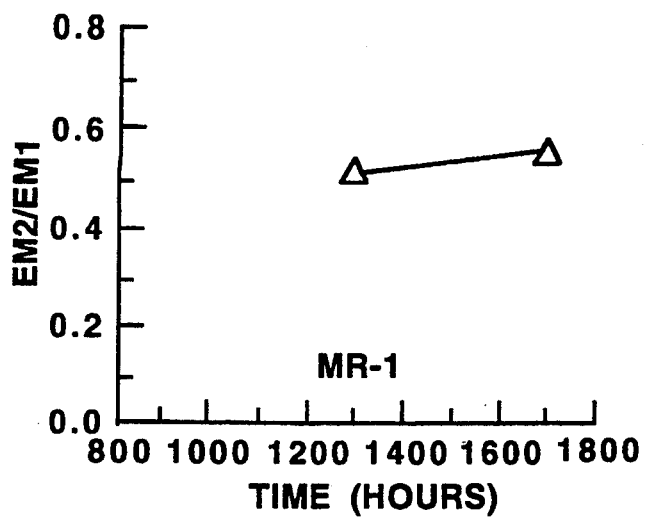
Figure 2E:
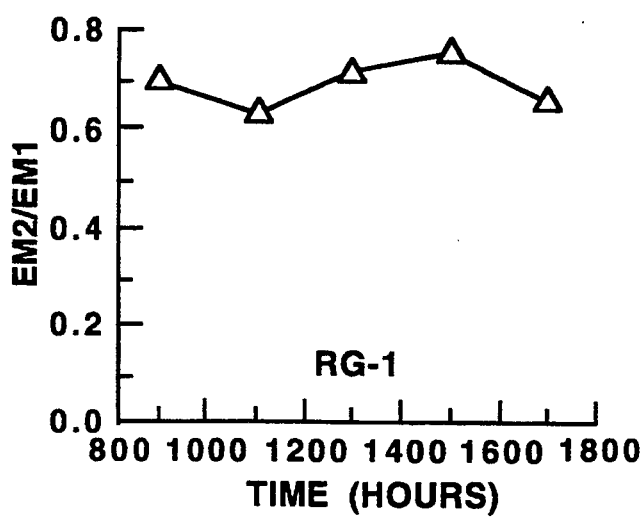
Figure 2F:
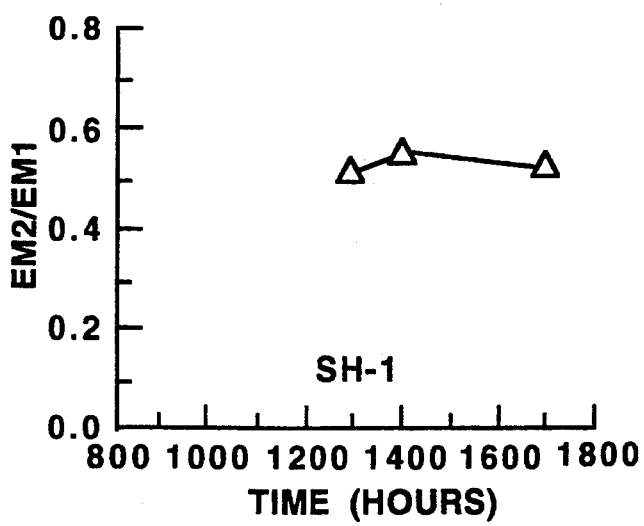
Figure 2G:
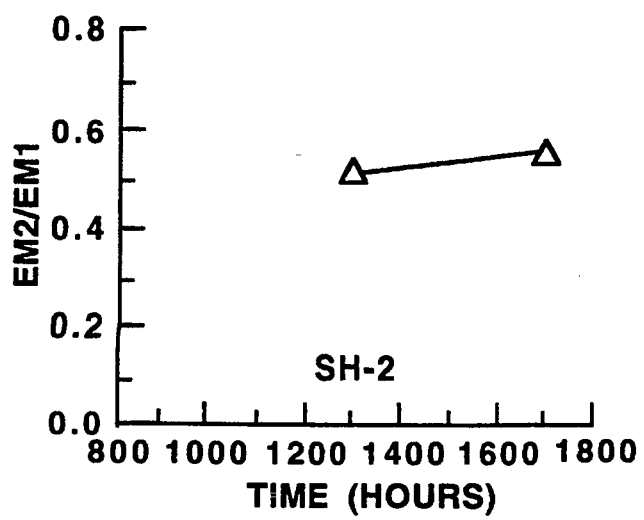
Figure 2H:
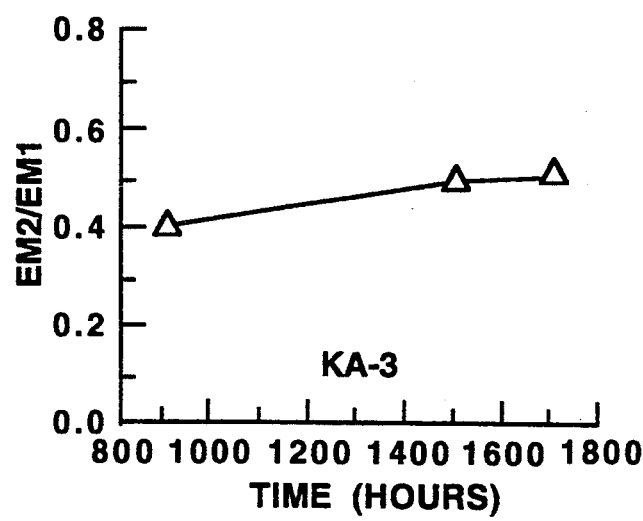

As used herein the terms "macromolecule" and "biopolymer" refer to molecules that are synthesized in biological systems, using discrete subunits as precursors.

A biopolymer is "formed from a subunit" if it is contains at least two identical subunits. Thus, a polypeptide is formed from a given amino acid subunit if it contains at least two residues of the given amino acid.

"Mass isotopomers" of a molecule are identical chemical structures which differ only in mass to charge ratio, or roughly, molecular weight, due to the presence of one or more selected mass isotopic atoms.

"Mass spectrometry" refers to an analytical tool by which one can separate and quantify molecules on the basis of their mass to charge ratio.

II. Method for Determining Isotopic Composition of the Subunit Pool

This section describes a method for determining the proportion of exogenously added biopolymer subunit precursor present in a specific biosynthetic pool in an organism. The general steps of the method are as follows:

(a) administering a subunit which is mass isotopically labeled, thereby to produce after a selected period of subunit incorporation, an enrichment of the mass isotopically labeled subunits in the biopolymer, (b) isolating the biopolymer from the subject after such incorporation period, (c) using mass spectrometry, determining the relative frequencies of at least two different mass isotopomers of the biopolymer which each contain at least one mass isotopically labeled subunit, and (d) calculating from such relative frequencies, the proportion of mass isotopically labeled subunit in the subunit pool from which the bioploymer was synthesized.

These steps are described below, and illustrated by reference to the method for determining acetyl-coenzyme A (acetyl-CoA) mass isotope enrichment in a human subject, as detailed in Example 1.

A. Administering Biopolymer Subunits to Subjects

1. Biopolymer Subunits

The biopolymer subunits which are administered are generally small molecules which are utilized in specific biosynthetic pathways, to produce polymeric macromolecules. As administered in the method of the invention, such subunits are mass isotopically labeled so that they can be distinguished from endogenous subunits. A variety of mass isotopically labeled subunits, such as mentioned below, are available from commercial sources, as given in the Examples. Such subunits can be labeled by substitution of any of the naturally occuring elements by an mass isotope of the elements. Mass isotopes which might be expected to be useful in mass isotope labeling of organic subunits include, but are not restricted to $^{13}C$, $^2H$, $^{18}O$, and $^{15}N$. It is desirable, in order to avoid metabolic loss of label, that the labeled atom(s) be relatively stable to metabolism or exchange within the subject. Typically the subunits contain one or more $^{13}C$ or $^2H$ atoms.

Such subunits may be metabolic precursors of the specific molecules used during polymeric synthesis; however, it is desirable that such precursor molecules not undergo extensive metabolism prior to use as subunits, in order to minimize dilution of the label present on the subunit.

Generally, in order to be measurable using the method of the invention, the macromolecule must be formed from repetitive building blocks, or subunits, as stated above. Furthermore, for accurate measurement, it is desirable that such a macromolecule be synthesized only once, completely, and as a discrete entity. Finally, it is desirable, for accurate measurement using the method of the invention that the core of the biopolymer not be rebuilt later, to minimize partial degradation followed by remodeling, since this would complicate the analysis.

The methods of the invention can be used to estimate isotopic composition of subunits in the subunit pool, as well as biopolymer synthesis kinetics, for any of a number of subunit precursor pools and associated biopolymers. Examples of subunit precursors and the biopolymers they form are listed in Table 1.

TABLE 1

Representative Biopolymer subunits

| Subunit | Biopolymer |
| --- | --- |
| acetate (acetyl coA) | cholesterol |
| acetate (acetyl coA) | fatty acids |
| ribonucleic acids | RNA |
| deoxyribonucleic acids | DNA |
| glucose | glycogen |
| amino acid | peptides/proteins |
| phosphoenol-pyruvate | glucose/UDP-glucose |
| glycine/succinate | porphyrin derivatives |

In studies carried out in support of the invention, rat and human subjects were given isotopically labeled acetate, a precursor of acetyl coenzyme A, and synthesis of fatty acid polymers was measured. In some experiments, subjects were also given sulfamethoxazole (SMX), a xenobiotic compound which undergoes acetylation in the liver using acetyl coenzyme A as donor. This reaction serves as an independent probe for acetate pools, to corroborate results obtained, using the method of the invention.

2. Administration of Biopolymer Subunits

Modes of administering the mass isotopically subunit may vary, depending upon the absorptive properties of the compound and the specific precursor pool into which the compound is targeted. Generally, an appropriate mode of administration is one that produces a steady state level of precursor subunit within the subunit pool and/or in a reservoir supplying such a pool. Intravenous or oral routes of administration are commonly used to administer such subunits; however, other routes of administration, such as subcutaneous or intramuscular administration, particularly when used in conjunction with slow release subunit compositions, are also appropriate routes. Compositions for injection are generally prepared in sterile pharmaceutical excipients.

In experiments carried out in support of the invention, and detailed in Example 1, human volunteers were administered mass isotopically labeled [1-$^{13}$C]or [2-$^{13}$C] acetate in saline as constant infusions 15 hours following a fasting period.

As will be seen below, the administering of mass isotopically labeled subunits to a subject is effective to produce, after a selected period of time, an enrichment of the mass isotopically labeled subunit in the biopolymer.

B. Isolating the Biopolymer and Determining its Isotopomer Frequency

This section will describe generally the process which biopolymer isotopomer frequency is measured in order to determine the proportion of mass isotopically labeled subunit in the subunit pool from which the bioploymer was synthesized.

1. Sampling Biopolymer

In practicing the method of the invention, biopolymer molecules are isolated from a subject according to methods known in the art and specific to the biopolymer of interest. Biopolymers of interest may be isolated from blood and/or tissue samples, according to the synthetic pool to be measured. In general, in order to determine a baseline mass isotopomer frequency distribution for the biopolymer, such a sample is taken before infusion of an isotopically labeled subunit precursor. Such a measurement is one means of establishing in the subject, the naturally occuring frequency of mass isotopomers in the biopolymer. When a subject is part of a population of subjects having similar enviromental histories, it is appreciated that a population isotopomer frequency distribution may be used for such a background measurement. Additionally, such a baseline isotopomer frequency distribution may be estimated, using known average natural abundances of isotopes. For example, in nature, the natural abundance in nature of $^{13}$C present in organic carbon is 1.11% (Deines). Methods of determining such isotopomer frequency distributions are discussed below. Typically, samples of the biopolymer are taken prior to and following administration of an isotopically labeled subunit precursor to the subject, and analyzed for isotopomer frequency as described below. Minimally, a single sample of isotopically enriched biopolymer (biopolymer synthesized subsequent to administration of isotopically labeled subunits) is sufficient for practicing the method of the invention.

With continuing reference to Example 1, sampling of enriched biopolymers (very low density lipoprotein (VLDL)-associated stearate and palmitate) was carried out at various time points during the infusion period, and samples were processed, as detailed in Example 1, to produce VLDL-associated fatty acid methyl esters (FAME). Biopolymer isotope enrichment was determined at each time point, as described below. FIG. 2 shows that excess mass biopolymer isotopomer ratios, determined as described below, remained substantially constant over time in a given subject.

2. Determining Mass Isotopomer Frequency for a Biopolymer

This section will describe the measurements and types of data analysis which are used to determine a mass isotopomer frequency for a biopolymer. According to an important aspect of the invention, described below, although the isotopomer frequency of the biopolymer may be expressed in a number of forms, in order to determine the proportion of mass isotopically labeled subunit in the biopolymer precursor subunit pool such mass isotopomer frequencies are optimally expressed as excess molar frequencies. Exemplary methods for calculating and expressing such frequencies are detailed in Example 4.

Generally, in order to determine the mass isotopomer frequency distribution for a biopolymer, the biopolymer sample is analyzed by mass spectrometry, using standard methods (Wolfe), and relative ratios of mass isotopomers are determined. As described in the exemplified method for FAME isotopomer analysis of Example 1, molecular anions m/z 298, 299, and 300 ($M_0, M_1, M_2$) for stearate-methyl ester (18:0) and m/z 270, 271, 272 ($M_0, M_1, M_2$) for palmitate-methyl-ester (16:0) were quantified by mass spectrometry.

Measured mass spectral peak heights may be conveniently expressed as ratios toward the parent (zero mass isotope) isotopomer for purposes of determining the relative frequencies of at least two different mass isotopomers of the biopolymer molecule. As will be appreciated from the ensuing discussion, the isotopomers analyzed will contain at least one mass isotopically labeled subunit, and, for purposes of comparison, it is convenient to express the mass spectral peak heights as ratios, using the peak height of the zero mass isotope parent compound as denominator, though it is appreciated that any calculation means which provides relative values for the abundances of such isotopomers in a sample may be used in describing such data, for the purposes of the invention.

With continuing reference to the exemplified method for analysis of fatty acid isotopomers detailed in Example 1, mass spectral peak heights were determined for $M_0$ (m/z 270 for palmitate methyl ester and m/z 298 for stearate methyl ester), $M_1$ and $M_2$ isotopomers to determine peak height ratio values $M_1/M_0$ and $M_2/M_0$ for each biopolymer. Generally, it will be appreciated that any number of peak height ratios $M_i/M_o$ can be determined, using the methods described.

In accordance with the method of the invention, isotopomer peak height ratios are expressed as a percentage total isotopomer content of the sample, or molar ratio. Although it will be appreciated that such molar ratios may be determined using any measurement system and algorithm which permits a comparison of mass isotopomers on a relative molar basis, such molar ratios are typically calculated using the sum of all measured isotopomer peak height ratios as denominator: Molar fraction $M_i/(M_0+M_1+M_2\ldots+M_n)$, where $M_i$ is the measured spectral peak height ratio of an isotopomer having i mass isotope containing subunits and n is the total number of subunits comprising the biopolymer, noting that $M_0=1$.

Figure 3A:
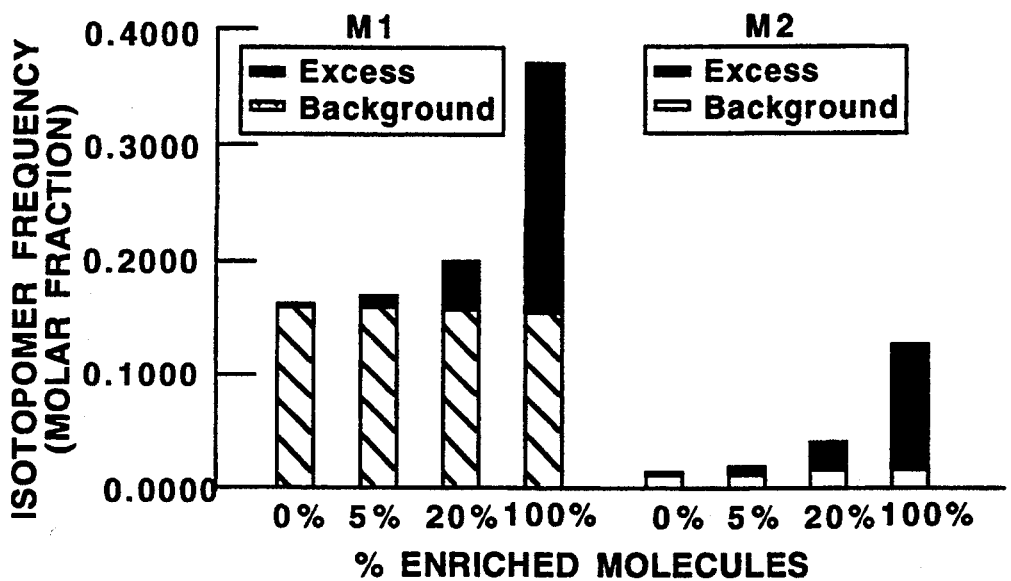
FIG. 3A is a bar graph showing the effect of varying fraction of new (isotopically enriched) biopolymer product molecules on molar frequencies and excesses for $M_1$ and $M_2$ isotopomers of palmitate methyl ester assuming a precursor subunit enrichment of p=0.06 (6.0 MPE)
Figure 3B:
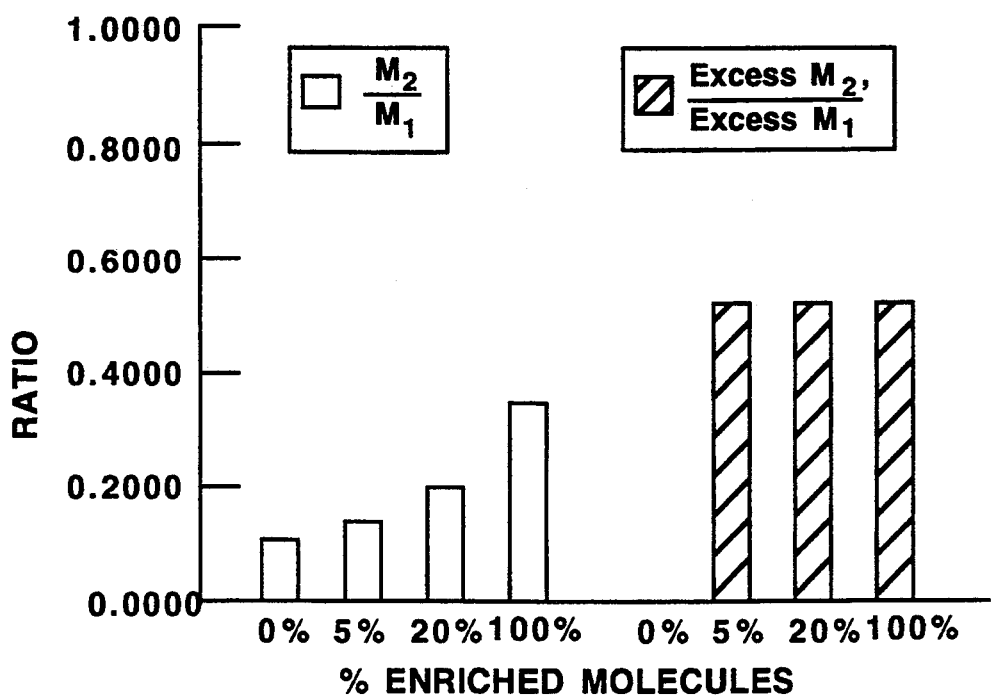
FIG. 3B is a bar graph showing the effects of varying fraction of new (isotopically enriched) biopolymer molecules on ratio of $M_2/M_1$ molar frequencies or $EM_2/EM_1$ molar excesses.

In accordance with an important aspect of the invention, it has been discovered that the ratio between excesses of different isotopomers, determined in relation to baseline levels of such isotopomers is not influenced by the fraction of molecules that is old or new (i.e., synthesized prior to or during labeled subunit administration, respectively). This relationship is derived and discussed in detail in Hellerstein (1991a) and in Example 4, herein. FIG. 3 illustrates the relationship, using acetyl-CoA excess molar frequencies (EM) and Excess molar ratios ($EM_i/EM_j$) determined for isotopomers as detailed in Examples 1 and 4, as described herein. It is appreciated that the invention described herein is not limited to the use of the specific equations shown in Example 4; rather, it utilizes generally the relationship of excess molar ratios between isotopomeric biopolymer species to determine subunit pool characteristics.

As detailed in Example 4, tables relating precursor subunit enrichment to molar fractions of $M_0$, $M_1$, and $M_2$ in a biopolymer can be generated using the algorithms described above. Table 5A is such a generated table. Similar distribution tables generated for cholesterol (analyzed as an underivatized fragment; Table 5B) and glucose (analyzed as glucose penta-acetate, synthesized from triose phosphate subunits; Table 5C), and are described in Example 4.

Figure 4A:
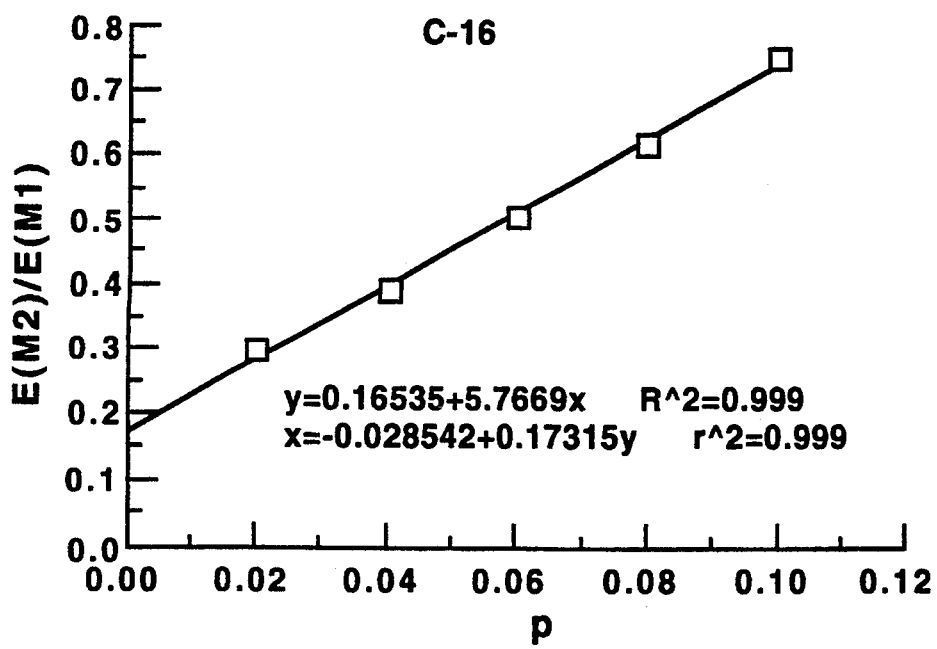
FIG. 4 shows the relationship between p (true precursor enrichment) and the ratio of $EM_2/EM_1$ for fatty acid methyl esters, palmitate (C-16, A) and stearate (C-18; B)

In summary, practice of the method of the invention is typically carried out as follows: The practioner first determines measured excess molar ratios for isolated biopolymer isotopomer species, as described in Examples. The practioner then compare measured internal pattern of excess ratios to the theoretical patterns. Such theoretical patterns can be calculated using the binomial or multinomial distribution relationships described in Example 4. Conveniently, the comparison of excess ratios can be carried out using a table, such as Table 5A, generated for a biopolymer of interest, or graphically, using determined relationships, as the relationships illustrated in FIG. 4 and as described in Example 4. From these comparisons, a value, such as the value p, is determined, which describes the probability of mass isotopic enrichment of a subunit in a precursor subunit pool. This enrichment value is then used to determine a value, such as the value $A_x^*$ described in Example 4, which describes the enrichment of newly synthesized biopolymers for each mass isotopomer, to reveal the isotopomer excess ratio which would be expected to be present, if all isotopomers were newly synthesized. Finally, in order to determine the fraction of polymers that were actually newly synthesized during a period of subunit administration, the practioner compares the measured excess molar ratio ($EM_x$) to above calculated enrichment value, $A_x^*$.

It can be seen from the above descriptions and from the examples provided herein, that subunit precursor pool composition can be obtained for a pool to which has been added an isotopically labeled subunit precursor by the steps of a) isolating isotopically labeled biopolymers, b) determining the enriched isotopomer species frequency distribution with reference to the background isotopomer species frequency to obtain isotopomer species molar excess ratios, and c) comparing such molar excess ratios to statistically determined molar ratios to determine a value, p, which describes the isotopic enrichment of the precursor subunit pool. These steps are summarized in FIG. 1A.

III. Method for determining synthetic rate of a. biopolymer

According to another aspect of the invention, rate of synthesis of a biopolymer can also be determined, according to another aspect of the invention, using the above-described characterization of biopolymer precursor subunit pools, when such synthesis involves incorporation of exogenously added isotopically labeled precursor subunits. Briefly, the method includes determining the proportion of mass isotopically labeled subunit present in the biopolymer subunit pool, as described in Section II, above, and using this proportion to calculate an expected frequency of a biopolymer containing at least one mass isotopically labeled subunit. This expected frequency is then compared to the actual, experimentally determined biopolymer isotopomer frequency. From these values can be determined the proportion of biopolymer which is synthesized from added isotopically labeled subunits during a selected incorporation period, as detailed in Example 2 for synthesis of VLDL-associated stearate in human subjects. Thus, the rate of synthesis during such a time period is also determined.

As described above, the methods described in the example are generally applicable to biopolymers as defined herein.

IV. Measuring Decay Rates of Biopolymer

In another aspect, the invention includes a method for measuring the rate of in vivo decay of a biopolymer which is formed from a subunit contained in a subunit pool in a subject.

In practicing the method, an isotopically labeled biopolymer subunit is administered to a subject, thereby enriching biopolymers formed from a subunit pool in mass isotopically labeled subunits, substantially as described above. In particular, the biopolymers are enriched in mass isotopomers containing multiple mass isotopically labeled subunits. These higher mass isotopomers of the biopolymers, e.g., biopolymers containing 3 or 4 mass isotopically labeled subunits, are formed in negligible amounts in the absence of exogenous subunit, due to the relatively low abundance of natural mass isotopically labeled subunit, but are formed in significant amounts during the period of biopolymer subunit incorporation from the enriched pool.

To determine decay rate, a biopolymer is isolated from the treated subject at two time points after administration. Preferably, the first time point is at least 2-3 hours after administration of subunit has ceased, depending on mode of administration, to ensure that the proportion of mass isotopically labeled subunit in the precursor pool has decayed substantially from its highest level following subunit administration. The following time points are typically 1-4 hours after the first time point but this timing will depend upon the replacement rate of the biopolymer pool.

The biopolymer taken from the subject at the sequential time points is analysed by mass spectrometry, to determine the relative frequencies of a high mass biopolymer isotopomer, defined above. Since the high mass isotopomer is synthesized almost exclusively before the first time point, its decay between the two time points provides a direct measure of the rate of decay of the biopolymer.

Figure 5:
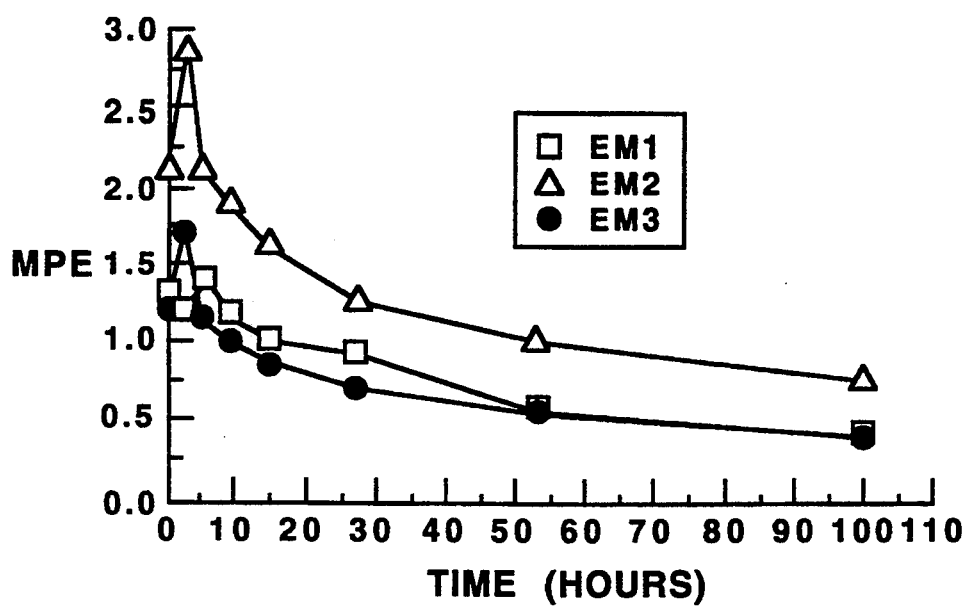
FIG. 5 shows decay curves for various mass isotopomers of cholesterol in a rat to which $[2-^{13}C]$-acetate was administered at time 0.

The method is illustrated in Example 5, which is concerned with the rate of decay of cholesterol in an animal subject, following mass isotope labeled with $^{13}C$-acetate, as described above. Labeled acetate was administered to the animal by IV infusion for a period of 12 hours. At times 0, 2.5, 5, 10, 15, 28, 50, and 100 hours after infusion ceased, blood sample was removed, and cholesterol isolated from each sample was analysed by mass spectrometry. FIG. 5 shows the time course of decay of frequency (amount, in MPE), of mass isotopomers of cholesterol containing either one (open triangles), two (open squares), or three closed circles) mass isotopically labeled acetate subunits. As seen from the figure, highest levels of incorporation of the labeled subunit into biopolymer occurred at 2.5 hours following the subunit administration, with decay of all isotopomers occuring at least over the next 50 hours.

The rate of decay of the biopolymer is determined from the decay curve for the three-isotope biopolymer (solid circles). In the present case, where the decay curve is defined by several time points, the decay kinetics can be determined by fitting the curve to an exponential decay curve, and from this, determining a decay constant.

While the invention has been described with respect to specific mass isotopes and biopolymers, it will be appreciated how the method can be used to determine subunit pool composition, and rates of synthesis and decay for substantially any biopolymer which is formed from two or more identical subunits which can be mass isotopically labeled.

V. Utility

The methods described herein are generally applicable to studying and diagnosing a number of biopolymer metabolic processes in human and animal subjects. It is appreciated that such methods are also applicable to isolated tissues, such as tumor tissues in which characterization of metabolic processes is desirable. Examples of medically relevant metabolic determinations which can be made, using the methods of the invention include: i) analysis of fat or cholesterol synthesis in an individual, to determine nutritional effects; ii) synthesis and breakdown of plasma proteins, as may occur in certain disease states; iii) muscle protein dynamics, to determine effects of such determinants as exercise, hormones and disease on synthesis and breakdown of muscle protein; iv) nucleic acid synthesis, including vital replication rates in vivo, for assessment of antiviral drugs on such rates in vivo, and DNA synthesis in a tumor, to determine the efficacy of chemotherapy; v) study of changes in gluconeogenesis, as may be affected by diseases such as diabetes, cancer and hypoglycemia.

The following examples illustrate specific methods of practicing the invention, but in no way are intended to limit the scope of the invention.

EXAMPLE 1

Sampling of Lipogenic Acetyl-Coenzyme A Pools in Human Subjects

A. Infusion of Isotopically Labeled Acetate into Human Subjects

Constant intravenous infusions of $[1-^{13}C]$ or $[2-^{13}C]$acetate were performed in human volunteers. A total of 16 infusions were performed in 11 subjects. All procedures and protocols were approved by the Committee on Human Research, University of California at San Francisco. Informed consent was obtained from subjects prior to studies. Sodium $[1-^{13}C]$acetate and $[2-^{13}C]$acetate are purchased from Isotec Inc. (Miamisburg, OH).

Subjects entered the General Clinical Research Center of the San Francisco General Hospital the morning of the overnight study. After 18:00 h, subjects were fasted (other than non-caloric beverages) until 09:00 the next morning. An intravenous line was place at 22:00 h, and at 02:00 h a constant iv infusion of $[1-^{13}C]$ or $[2-^{13}C]$acetate (1.16-1.69 mmol/kg/min) in 0.45% saline was begun. Oral doses of 750 mg sulfamethoxazole (SMX) were given at 02:00 and 07:00 h, then 500 mg doses at 11:00 and 15:00. All urine voids were collected after 02:00, and aliquots from each were saved (urine was not pooled). At 08:00, a heparin lock was placed in the contralateral arm for blood drawing, and hourly blood samples were taken until 17:00 h. At 09:00 refeeding was begun with an hourly oral liquid mixed meal (Ensure ®), to deliver carbohydrate at 7 mg/kg/min (consisting of 85% glucose and 15% fructose). This was continued through 17:00. After 17:00, the study ended. Three to five days prior to an infusion study, subjects received a dose of oral SMX (750 mg) followed by urine collected for 5 hours, to provide a baseline SMX-acetate sample for comparison to enriched samples.

B. Isolation and transesterificaton of Very Low Density Lipoproteins (VLDL)

Plasma VLDL was prepared by ultracentrifugation. Two ml of plasma were mixed with 4 ml of a 1.0063 g/ml NaCl-EDTA solution ("mock") in a polycarbonate ultracentrifugation tube (Beckman, Palo Alto, CA). Prior to VLDL isolation for subjects refed orally, chylomicrons were removed by a 30-min centrifugation at 33.200 rpm at 17° C. (Beckman, model L2-65B ultracentrifuge). The upper 1 ml of the mock cushion (0-1 ml fraction) containing chylomicrons was aspirated by glass pipette. One ml of fresh mock was added and mixed with the remaining 5 ml of cushion before ultracentrifugation. VLDL was isolated by a 17-h 40,000 rpm spin at 17° C. The 0-1-ml fraction containing VLDL was aspirated by glass pipette. A 100-μl aliquot was used for triglyceride (TG) quantification (Nagele). The remaining 900 μl was stored at −20° C.

Lyophilized VLDL was resuspended in 3.75 ml 2:1 (w/v/) methanol/chloroform mixture followed by shaking at 4° C. Samples were centrifuged and supernatants were decanted into clean glass centrifuge tubes. The pellet was washed with 4.75 ml 2:1:0.8 (v/v/v) methanol/chloroform/water mixture which was then aspirated and added to the supernatant. The residual pellet was discarded, and 2.5 ml each of chloroform and water were added to the combined extraction mixtures. Following centrifugation, the chloroform phase containing released VLDL-TG was extracted into a clean centrifuge tube and dried under nitrogen gas. TG was stored at −20° C.

Fatty acids (FA) in VLDL-TG were trans-esterified in methanolic-HCl (Christie), and the Fatty acid methyl esters (FAME) were analyzed by gas chromatography/MS. TG samples were resuspended in 1 ml chloroform and 5% methanolic HCl (Supelco, Inc.). The mixture was incubated and shaken for 2 h at 50°-60° C., then 2 ml of 5% aqueous NaCl were added. FAME were extracted by 2×5 ml of hexane washes. The combined hexane extracts were washed with 4 ml of 2% potassium carbonate which is removed from hexane by glass pipette aspiration. Anhydrous sodium sulfate was added to the washed hexane extract. Following centrifugation, the hexane supernatant was decanted into a clean centrififuge tube and dried under nitrogen gas.

C. Gas chromatography/Mass Spectrometry (GC/MS) analysis of plasma VLDL-FA

FAME were analyzed using an HP model 5970 gas chromatogrpahy MS (Von Schaky). Conditions were isothermal (200° C.) with a 20-meter fused silica column. Molecular anions m/z 298, 299,and 300 (M0, $M_1$, $M_2$ for stearate-methyl ester (18:0) and m/z 270, 271, 272 ($M_0$, $M_1$, $M_2$) for palmitate-methyl-ester (16:0) were quantified. Excess enrichment was calculated as described below relative to true baseline (unenriched) samples for each subject.

D. Determination of Excess Mass Isotopomer Frequency ratios in VLDL-fatty acids

Measured mass spectral peak heights were expressed as ratios toward the parent (zero mass isotope) isotopomer (m/z 270 for palmitate methyl ester and m/z 298 for stearate methyl ester) to give a value $M_i$, where i varies from 0 to the total number of subunits present in the isotopomer, n. Measured molar ratios were then calculated using the sum of all measured isotopomer peak height ratios as denominator: Molar fraction $M_i/(M_0+M_1+M_2\ldots+M_n)$, where $M_i$ is the measured spectral peak height of an isotopomer having i mass isotope containing subunits and n is the total number of subunits comprising the biopolymer, noting that $M_0=1$.

For purposes of illustration, in an exemplary subject, natural abundance (baseline) mass spectral (MS) values were determined: $M_1/M_0=0.1960$ and $M_2/M_0=0.0220$. Background molar fractions were determined as follows for each isotopomer $$M_1/(M_0+M_1+M_2) = 0.1960/1.2180 = 0.16092$$

$$M_2/(M_{0pi}+M_1+M_2) = 0.0220/1.2180 = 0.01806$$

The subject's VLDL-palmitate was isolated 4 and 8 h after refeeding was begun, during a constant infusion of [2−$^{13}$C]-acetate (1.40 mmol·kg$^{-1}$·min$^{-1}$). The palmitate-methyl ester was analyzed by MS as follows: at 4 h $M_1/M_0$ is equal to 0.2131 and $M_2/M_0$ is equal to 0.0291. Therefore $$M_1/(M_0+M_1+M_2)=0.2131/1.2422=0.17155$$

$$M_2/(M_0+M_1+M_2)=0.0291/1.2422=0.02343$$

Excess molar frequencies (EM) and Excess molar ratios ($EM_i/EM_j$) were then determined for isotopomers as follows:

$$EM_2=0.02343-0.01806=0.00536$$

$$EM_1=0.17155-0.16092=0.01063$$

FIG. 2 shows plots of the ratios $EM_2/EM_1$ isotopomer frequencies over time during infusions of [1-$_{13}$C]- or [2-$_{13}$C] acetate in several subjects, showing that such ratios were fairly constant values at plateau. This ratio was then used to calculate the true precursor enrichment of the acetyl-coA pool, p, by comparison to a statistically generated probability distribution describing the probability of each subunit being labeled, as described in Example 4. Table 5A shows a table generated for use in determining acetyl-CoA precursor pool composition for palmitate methyl ester, and described in further detail in Example 4.

From these manipulations, a calculated p =0.0588 =5.88 MPE is derived for the data described.

At 8 h, $M_1/M_0$ was equal to 0.2237, and $M_2/M_0$ was equal to 0.0338. Therefore $$(M_1/M_0)/(M_0+M_1+M_2=0.2237/1.2575=0.17789$$

$$(M_2/M_0)/(M_0+M_1+M_2)=0.0338/1.2575=0.02688$$

$$EM_2=0.02688-0.01806=0.00882$$

$$EM_1=0.17789-0.16092=0.01697$$

$$EM_2/EM_1=0.5197$$

$$\text{calculated } p=0.0614=6.14 \text{ MPE}$$

For this subject, measured SMX acetate enrichment at hours was 6.05 MPE, calculated as described by Hellerstein et al., as an independent confirmation of the above derived acetyl-coA pool enrichment. This relationship, between acetyl-coenzyme A pool enrichment determined using the biopolymer mass isotopomer frequency distribution of the invention and acetyl-coenzyme A pool enrichment using the SMX acetate method has been described (Hellerstein et al, 1991b)

Table 1 shows for VLDL-stearate (C-18) isotopomer frequencies and calculated true precursor enrichment values (shown as MPE) for 16 subjects. C-16 isotopomer data is also shown.

EXAMPLE 2

Measurement De Novo Synthesis of palmitate and stearate

A. Measurement of acetyl-CoA precursor pool enrichment

Normal human subjects were infused with [1-$^{13}$C] acetate during fasting and refeeding, essentially as detailed in Example 1, except that subjects were refed with (i) ENSURE (hourly from 0900-1700 hours), (ii) a single breakfast at 0900 h (3.5 g of carbohydrate/kg of body wt, 20–25 g of protein, 15–20 g of fat), or (iii)

glucose infusion (7–10 mg/kg from 0900–1700 hours), as described in Hellerstein (1991b). True acetyl-CoA precursor enrichment, p, was determined, using the copolymer mass isotopomer frequency distribution method of the invention, corraborated by the SMX-acetate method (Hellerstein, 1991a). The maximum possible frequency of the $M_1$ biopolymer isotopomer (mass isotope) relative to the sum of $M_0$ (zero isotope) and M1 isotopomers was calculated from the p value, using the relationship shown in FIG. 4. VLDL-FA enrichment (MPE) was measured for [$(M_1/(M_0+M_1)$]using the method described in Example 1.

B. Calculation of de novo synthesis

Percentage of each (C-16 and C-18) VLDL-FA biopolymer derived from the de novo pathway (percent de novo lipogenesis) was calculated using the precursor-product relationship:

VLDL-FA enrichment/$A_1$*.

Results of these studies are summarized in Table 2.

C. Example Calculation of de novo synthesis

An example of the method for calculating de novo lipogenesis for VLDL-stearate follows. If infusion of [$^{13}$C]acetate results in an acetyl-CoA enrichment of 7.0 MPE and natural abundance of acetate is assumed to be 2.22%, the ratio of $M_1/(M_0+M_1)$ isotopomers before and after administration of tracer will be:

$$\text{Back-ground} \frac{(M+1)}{(M+0)+(M+1)} = \frac{b(1; 9, 0.022)}{(b(0; 9, 0.022) + b(1; 9, 0.022)} \quad (2)$$

$$= \frac{0.1657}{0.8186 + 0.1657}$$

$$= 0.1683$$

$$\text{Enriched} \frac{(M+1)}{(M+0)+(M+1)} = \frac{b(1; 9, 0.092)}{b(0; 9, 0.092) + b(1; 9, 0.092)} \quad (3)$$

$$= \frac{0.3826}{0.4195 + 0.3826}$$

$$= 0.4770$$

$$\text{Excess} \frac{(M+1)}{(M+0)+(M+1)} = 0.4770 - 0.1683 = 0.3087 \quad (4)$$

This can be readily translated into kinetic terms. At time zero, the ratio of $(M_1)$ abundance relative to $M_0+M_1$ is 0.1683 in VLDL-stearate. If all VLDL-stearate were then replaced by newly synthesized molecules derived from acetyl-CoA during the experiment, $M_1/M_0+M_1$ would increase to 0.4770, or the excess, termed $A_1$* would be 0.3087. If only 50% of VLDL-stearate were derived from acetyl-CoA and the remainder were from reesterification of preformed stearate, $A_1$* would be half-way between 0.1683 and 0.4770 (0.3227), or the excess would be half of $A_1$*. If only 10% of stearate came by way of acetyl-CoA, the observed excess would be one-tenth of $A_1$*; and so on. The value for A, is precisely analogous to the standard relationship between product and precursor specific activity or enrichment used in fractional synthesis calculations (Waterlow).

Accordingly, calculation of fractional VLDL-FA synthesis from acetyl-CoA during an experiment can be made. The measured enrichment in the FA ($EM_1$) is divided by the calculated asymptotic ("precursor") value, $A_1$. The latter is calculated from the equation relating *p to $A_1$* (FIG. 5). SMX-acetate enrichments were used to confirm hepatic acetyl-CoA enrichments (p).

EXAMPLE 3

Measurement of Cholesterol Synthesis

A. Chemicals and Isotopes

Sodium [I-$^{13}$C]and [2-$^{13}$C]acetate (>98% enriched) were purchased from Isotec, Inc. (Miamisburg, OH). High purity ethyl ether and chloroform were used for extractions leading to isotope ratio (IR)/MS analyses (<1 ppm carbon residues).

B. Sample Preparation and Mass Spectrometry (MS)

Cholesterol (C) was extracted from 100 μL of serum with 2 ml of 95% ethanol:acetone (1:1, v:v). The trimethyl-silyl derivative of free C was formed using N,O-bis-(trimethylsilyl)-trifluoroacetamide with 1% trimethylchlorosilane. C-E is not derivitized by this technique. Gas chromatography/mass spectrometry (GC/MS) analysis was with an HP Model 5970 GC/MS (Hewlett Packard Co., Palo Alto, CA), using a 15 meter DB-1 column. Conditions were isothermal at 275° C. using split injection under electron impact ionization and selected ion recording. The parent $M_0$ peak (m/z 368 representing underivitized cholesterol minus [—OH]was monitored as were $M_1$ to $M_4$ (m/z 369 to 372). Molar excesses (enrichments) were calculated by subtraction of true baseline samples.

For IR/MS analysis of free C, 1 ml of serum was extracted with 4 ml of isopropyl alcohol:heptane (70:30, v:v), vortexed and acidified with 2 ml of 0.033M $H_2SO_4$. The organic phase was apsirated and dried. The dried lipid was resuspended in 60 μL chloroform and separated by thin layer chromatography (TLC), using Silica-Gel G TLC plates (Analtech, Newark, DE). Free C was identified using chlosterol standards (Sigma, St. Louis, MO) under iodine vapor. After scraping the plates, free C was extracted from the silica support using high purity ethyl ether (2×1 ml extraction) then washed with water and dried under $N_2$. This was brought up in 20 μL chloroform (high purity) and transferred to tin capsules. Preliminary studies showed significant dilution of labeled standards containing known $^{13}$C-enrichments when non-highly purified ethyl ether was used for extractions. Accordingly, only highly purified solvents were used and extraction volumes were kept to a minimum. Using this strategy, total carbon yields from serum free C were in the range of 100 μg or greather. After allowing the chloroform to evaporate, the tines were placed in a lyophilizer for 15 min to ensure total removal of chloroform. The cholesterol $^{13}$C content was then analyzed by IR/MS (Roboprep/Tracermass; Europa Scientific, Crewe, UK). Briefly, this instrument consists of an automated sample introducer, Dumas combustion column, drying tube, and gas chromatography (21b), followed by an IR/MS. The ratio of $^{13}$C/$^{12}$C (m/z 45 and 44, respectively) is calculated by comparison with standards. Natural adundance cholesterol was analyzed using National Bureau of Standards citrus leaves (#1572) as reference (1.08144 $^{13}$C). Enriched samples were analyzed using International Atomic Energy Association calibration standard #309A (1.21431% $^{13}$C) as reference.

Enrichment of urinary sulfamethoxazole-acetate (SMX-acetate) was measured as described in detail elsewhere (Hellerstein, 1991a). Briefly, SMX-acetate was isoalted from urine by HPLC using a reverse-phase C-18 Resolve column (Waters Inc., Milford, MA). The SMX-acetate peak was collected, lyophilized, and analyzed by HPLC/MS using a VG30-250 quadrupole mass spectrometer (VG Masslab, Altrincham, Cheshire, UK) linked to a Waters 600 Multisolvent Delivery System (Waters/Millipore, Millford, MA) via a VG thermospray interface. The molecular anion [M-H]- and isotope [M +1 - H]are monitored (m/z 296 and 297).

C. Rat Infusion Protocols

Male Sprague-Dawley rats were catheterized using indwelling intrajugular silastic catheters placed under metaphane anesthesia, tunneled out through the interscapular area and protected by a flexible spring housing. Animals resumed normal food and water intake within 24–48 hr after catheterization. Sodium [1-$^{13}$C]or [2-$^{13}$C]acetate was infused at 1.25 mmol/kg/hr from midnight until noon. Sulfamethoxazole infusions were begun at 07:00 with an iv bolus of 40 mg/kg followed by a constant infusion at 40 mg/kg/hr until noon. Animals were anesthetized with sodium pentobarbital IV (50-100 mg/kg) at noon, inferior vena cava blood was drawn and the animals were exsanguinated. In certain animals, a decay curve was generated by sequential blood drawing (300–500 μL blood per draw) through the indwelling catheter.

D. Human Subjects and Infusion Protocols

Normal women were recruited by advertisement. All protocols were approved by the University of California at San Francisco Committee on Human Research. Informed consent was obtained in all subjects prior to enrollment. Five women between the ages of 20–40 were studied during the follicular (pre-ovulatory) phase of their menstrual cycles. All subjects habitually consumed standard, nonvegetarian diets. Sodium [1-$^{13}$C]or [2-$^{13}$C]acetate was infused at 0.072-0.123 mmole/kg/hr from 0.2:00 until 17:00 during an overnight fast followed by a refeeding protocol consisting of hourly ingestion of a liquid mixed meal (Ensure®) between 09:00 and 17:00, as described previously (20). The liquid meal contained 30% calories as fat, 45% as glucose, 8% as fructose, and 17% as protein and was ingested to deliver a rate of 7 mg carbohydrate calories/kg/min over 8 hours. The total cholesterol content administered over the 8 hr refeeding period was 0.357 mg/kg (about 21 mg for a 60 kg subject). Sulfamethoxazole was administered orally as described elsewhere (20, 18). Blood was drawn every other hour from 09:00 through 17:00. A decay curve was generated after the labeled acetate infusions were discontinued at 17:00 by analysis of blood samples taken at 18:00, 20:00, 22:00, 24:00 than 08:00 on days 2, 3 and 4.

E. Calculations

A statistical method is described in detail in Example 4. To summarize, in the context of chlolesterol biosynthesis, the enrichment of the acetate units that entered newly synthesized circulating cholesterol molecules was calculated from the isotopmer frequency pattern in cholesterol (Table 3). The fraction of serum cholesterol molecules that were newly synthesized during the experimental period was then calculated by comparison of measured isotopomer frequencies ($EM_x$) to the calculated isotopomer frequency in newly synthesized cholesterol molecules ($A_x^*$, Table 3). During the period after cessation of label incorporation, the rate constant of decay of higher mass isotopomers ($M_2$-$M_4$) of cholesterol is determined, to exclude ongoing label incorporation. By combining the label incorporation data (rate of accumulation of newly synthesized serum cholesterol molecules) with the label exit data (rate constant of labeled cholesterol removal from serum) and an estimate of body free C pool size in accordance with appropriate equations described in Example 4, the absolute endogenous synthesis rate of serum cholesterol was calculated. The non-steady state equation was used:

$$\#(1) K = k \cdot B / 1 - e^{kt},$$

where

B (mg)=mass of newly synthesized cholesterol molecules=f·(pool size), f (%)=fraction of circulating cholesterol derived from endogenous synthesis =$EM_x/A_x$, pool size =9 g in humans and a proportional value ( 130 mg/kg) in rats, K (hr$^{-1}$)=rate constant of isotopic cholesterol decay, and K (mg/hr): absolute rate of endogenous serum cholesterol synthesis.

Calculation of Contribution During Refeeding

Because the infusion protocol consisted of sequential fasting/refeeding phases, the new contribution during the refeeding phase had to be corrected for incorporation during the preceding fast. This was calculated by assuming that labeled free C present after the fasting phase decayed according to the measured rate constant of decay (k). Accordingly, new synthesis after refeeding was the difference between the measured (net or combined) fractional synthesis and the value that would have been present if no incorporation had occurred during refeeding:

$$\#(2) f_{(new)} = [f_{(refeed)}] - [f_{(fasted)} \times e^{-kt}]$$

EXAMPLE 4

Calculation Of Relationship between Precursor Enrichment Ratio of Excess $M_2$/Excess $M_1$ Isotopomer Frequencies in Biopolymer Molecules A. Model for Calculation of Natural Abundance and Enriched Isotopomer Frequencies in a Polymer In order to determine isotopomer frequencies for a biopolymer, the biopolymer product derived from subunits or subunit precursors was considered be a chain of precursor units of length n. For fatty acids (FA) as described in Example 1, the administered subunit precursor was acetate and n is 8 for palmitate, 9 for stearate, etc. Both in the natural abundance (unenriched) state and after experimental introduction of [$^{13}$C]acetate into the precursor pool, each FA will include a certain frequency of $M_0$, $M_1$, $M_2$, etc. isotopomers. The frequency of each isotopomer species is a function of the isotopic abundance of $^{13}$C in acetate units at the time of FA synthesis and n, as described by the binomial distribution:

$$F(M_x) = b(x; n, p) = [^n x](p)^x (1-p)^{(n-1)} \qquad (4)$$

where F =frequency of an isotopomer in a polymer (molar fraction), n =number of units in the polymer, x =number of labeled ("special ") units in the polymer, p =probability of each unit being labeled, and $$\begin{bmatrix} n \\ x \end{bmatrix} = \frac{(n)!}{(n-x)!(x)!}$$

Thus, for a palmitate molecule containing acetate units with natural abundance $^{13}C$ in acetate ( 0. 022 ), the molar frequencies of $M_0$, $M_1$, and $M_2$ were calculated as:

$F(M_0) = b \ (0; \ 8, \ 0.022) = [^8_0](0.978)^8 = 0.8370$ $F(m_1) = b(1; \ 8, \ 0.022) = [^8_1](0.022)^1 \ (0.978^7 = 0.1506$ $F(M_2) = b \ (2; \ 8, \ 0.022) = [^8_2](0.022)^2 \ (0.978)^6 = 0.0119$

By way of numerical example, if a $^{13}C$ enrichment of 6.0 molar percent excess (MPE) is introduced into the acetyl-CoA precursor pool, the $^{13}C$ abundance becomes 0.082 and the isotopomer molar frequencies in newly synthesized palmitate molecules become, $F(M_0) = b(0; \ 8, \ 0.082) = [^8_0](0.918)^8 = 0.5044$ $F(M_1) = b \ (1; \ 8, \ 0.082) = [^8_1](0.082)^1 (0.918)^7 = 0.3604$ $F(M_2) = b \ (2; \ 8, \ 0.082) = [^8_2](0.082)^2 (0.918)^6 = 0.1127$ In practice, the contributions from rare Mhd 2 acetate units (containing $^{13}C$ in both carbons), $^{18}O$ and the derivitizing (methyl) group also have to be considered, although these are relatively small inputs, as described in detail in Example 7. Using the binomial equations described above and in Example 7, tables relating precursor (acetyl-CoA) enrichment to molar fractions of $M_0$, $M_1$, and $M_2$ in palmitate- and stearate-methyl esters were generated (such Table 5A for palmitate methyl ester).

In Table 5A, the first column, p, represents the probability that the precursor subunit pool is isotopically enriched, where p=0.000 represents zero enrichment or natural abundance in the precursor subunit. It can be seen from the table that when p=0.000, there exists a calculable isotopomer distribution in the biopolymer. This p=0 distribution represents a theoretical baseline isotopomer distribution, which may be subtracted from other distribution values to generate excess values.

Columns headed "$A^x$" represent the theoretical excesses for determining different mass isotopomers (enriched molar frequency minus baseline molar frequency), as a function of p. These values represent theoretical polymers which are synthesized entirely (100%) from precursor subunits in a subunit pool having an enrichment value, p. Accordingly, these values represent the mathematical asymptote (A) that would be approached for each isotopomer as baseline unenriched biopolymers are replaced by enriched biopolymers. Thus, $A_1^*$ is the asymptote or 100% newly synthesized value for the $M_1$ isotopomer of the polymer; $A_2^*$ for the $M_2$ isotopomer, etc.

The columns headed "R" contain the internal ratios among theoretical molar excesses as a function of p (i.e, $A_2^*/A_1^*$, for p=0.05). As described as a part of the present invention, such internal ratios are independent of the mixture of baseline and enriched polymers present; that is, they are uniquely characteristic of the newly synthesized molecules, independent of the proportion, such newly synthesized molecules represent in the mixture. The internal or distribution pattern thereby allows the practioner to locate in the table an $A_x^*$ value from an experimentally determined excess ratio, R, and thereby, to determine the proportion of newly synthesized molecules that would be expected, if all biopolymer molecules were derived from new synthesis (i.e., synthesis occuring subsequent to administration of the isotopically enriched subunit).

The theoretical isotopomer distributions correspond well with measured natural abundance isotopomer frequencies in palmitate-methyl ester and stearate-methyl ester as detailed by Hellerstein (1991a). Table 5B is a partial table generated as above, for cholesterol analyzed as an underivatized fragment minus-OH synthesized from [2-$^{13}C$]-acetyl-coA precursor subunits, and Table 5C is generated for synthesis of glucose, analyzed as glucose pentaacetate, synthesized from triose phosphate precursors.

B. Relationships Between Precursor Enrichment and Excess Isotopomer Ratios

The isotopomeric frequency distribution in a FA, or any polymer consisting of a discrete number of $^{13}C$-labeled precursor units, will be uniquely determined by the $^{13}C$ abundance of the biosynthetic precursor. This has two important implications. First, calculations of synthesis (fraction of new molecules added over a time period) have to take this isotopomeric distribution into account (see below). Second, if the isotropic enrichment of a precursor (p) is uniquely represented by the isotopomeric frequency distribution in its polymeric product, this can be exploited as a way of inferring the enrichment of the true biosynthetic precursor without having to isolate biochemically the anatomic precursor molecule. With reference to the data of Example 1, after an infusion of [$^{13}C$]acetate, circulating VLDL-FA consists of a mixture of previously present (preformed) FA, and newly synthesized VLDL-containing de novo synthesized FA. Only the last of these will reflect the acetyl-CoA precursor pool enrichment during the [$^{13}C$]acetate experiment. Therefore, it is useful to describe isotopomeric frequencies in mixtures in which less than 100%, such as 5 or 20%, of the VLDL-FA were synthesized de novo during the subunit administration period.

One solution to the problem of such mixtures consists of using excess isotopomer frequencies. Because the isotopomeric composition of the mixture is a linear combination of its components, the fraction of FA molecules that are new (enriched) or old (unenriched) will influence the absolute abundances of each isotopomer species. By expressing isotopomer frequencies as excesses relative to natural abundance values, however, only new, enriched molecules contribute. The ratio between excesses of different isotopomers is therefore not influenced by the fraction of molecules that are old or new. This is demonstrated with a numerical example, illustrated in FIG. 3, using acetyl-CoA enrichments of 0.06 and 0.08 with 0 (natural abundance), 5, 20, and 100% palmitate molecules derived from de novo lipogenesis (enriched). The ratio of excess $M_2$/excess $M_1$ frequencies is constant over the range of mixtures, whereas the ratio of absolute $M_2/M_1$ frequencies was greatly influenced by the composition of the mixture. It should be noted that the difference between binomial expansions (natural abundance distribution subtracted from enriched distribution) is not itself described by a binomial expansion. It is, however, characteristic for a precursor enrichment and can be interpreted graphically (FIG. 4).

Figure 4B:
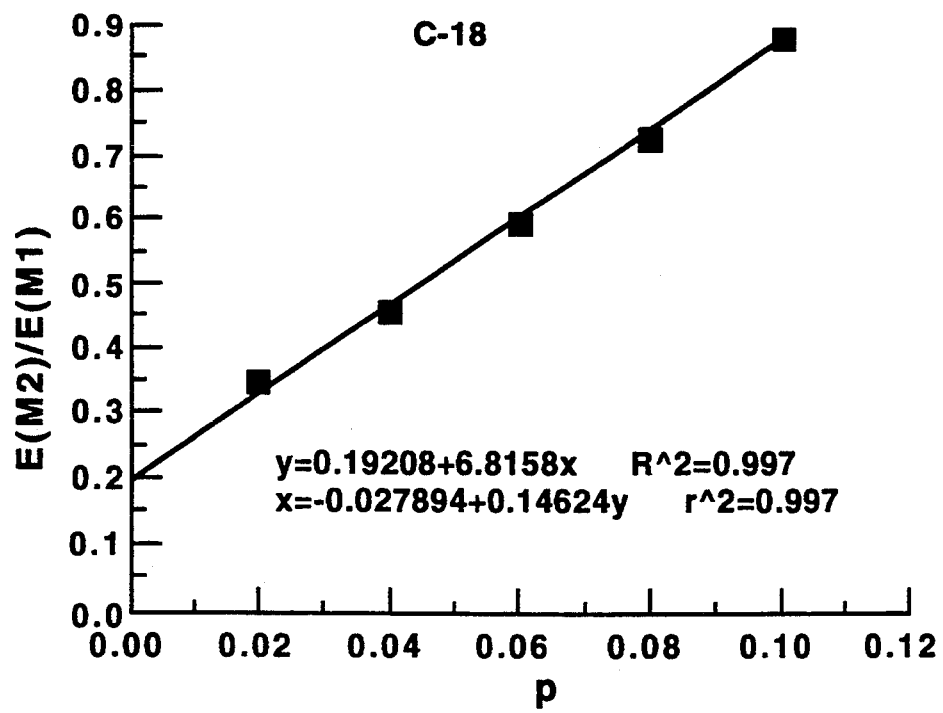

Because the excess M$_2$/excess M$_1$ ratio is independent of the fraction of molecules that are enriched, a single equation relating precursor enrichment (p) to excess M$_2$/excess M$_1$ ratios in palmirate-methyl ester and a single equation for stearate-methyl esters is sufficient, as illustrated in FIG. 4. These equations apply equally to any mixture of background and enriched molecules. It is worth noting that the relationship between p and excess M$_2$/excess M$_1$ ratios is linear, between p=0.02 and p=0.10. This relationship can be used to analyze subunit enrichment, when such subunit enrichment changes over the course of an experiment or when more than one pool contributes subunit (i.e., if there is hepatic and extrahepatic synthesis, as might occur for cholesterogenesis). Because the relationship is linear, the average p will be reflected in the excess M$_2$/excess M$_1$ ratio. If, for example, 75% of enriched molecules came from a pool at 0.05 enrichment excess M$_2$/excess M$_1$=0.4537 while 25% were from a 0.07 enriched pool excess M$_2$/excess M$_1$ =0.569 the average p should be 0.055 and this in fact could be inferred from the excess M$_2$/excess M$_1$ ratio of the mixture (0.4825), using the regression equation for C-16 (FIG. 4B).

EXAMPLE 5

Measurement of Decay of Isotopically Labeled Cholesterol In Vivo

Male Sprague-Dawley rats were catheterized with indwelling intrajugular silastic catheters under metaphane anesthesia. The catheters were tunneled out through the interscapular area and protected by a flexible spring housing. Animals resumed normal food and water intake within 24–48 hr after catheterization. Sodium [1-$^{13}$C]or [2-$^{13}$C]acetate was infused at 1.25 mmol/kg/hr from midnight until noon. Sulfamethoxazole infusions were begun at 07:00 with an iv bolus of 40 mg/kg followed by a constant infusion at 40 mg/kg/hr until noon. Animals were anesthetized with sodium pentobarbital IV (50–100 mg/kg) at noon, inferior vena cava blood was drawn and the animals were exsanguinated. A decay curve was generated by sequential blood drawing (300–500 μL blood per draw) through the indwelling catheter.

The fraction of circulating free C attributable to endogenous synthesis was determined as shown in Table 5, wherein P (MPE) was calculated from the ratios of EM$_1$/EM$_{1-4}$ and EM$_3$/EM$_{1-4}$, using Table 3. In adlibitum fed rats (n = 12), fractional synthesis was 2.89 ±0.44% after 12 hr of labeled acetate infusion. Recombinant TNF, which has been shown to stimulate hepatic cholesterogenesis using the $^3$H$_2$O technique, increased fractional cholesterol synthesis in rats 4-fold (Table 5).

Serial time points were collected from rats after completion of the labeled acetate infusions. The enrichments of individual mass isotopomers were plotted over time (FIG. 6). The apparent rate constant of decay using EM$_1$ was smaller than for higher masses and incongrous late increases in EM$_1$ were sometimes observed (not shown), consistent with persistent incorporation of $^{13}$C into the M$_1$ isotopomer of cholesterol but not the higher mass isotopomers.

EXAMPLE 6

Measuring Fat Synthesis in an Obese Subject

An obese human subject was studied by administration of sodium [2-13C]-acetate intravenously, in order to establish whether synthesis of new fat by his body was contributing to his adiposity, or whether his body fat came from dietary fat. VLDL-palmitate was isolated from his blood, the palmitate-methyl ester was formed and the method as described in example 1 was applied. Results are shown in FIG. 6. Peak heights of masses 270,271 and,272 were measured and peak height ratios calculated(columns C and D). Baseline mass isotopomer frequencies were subtracted to calculate molar excesses(columns M and N). The internal ratios of EM2-/EM1 were calculated (column Q),from which values of the precursor acetyl-CoA pool isotope enrichment (p) were calculated (column S), using the statistically-calculated relationship between acetyl-CoA precursor pool enrichment and palmitate-methyl ester isotopomer composition shown in table 5A and FIG. 4A. Based on these values for p, the expected frequency of mass isotopomer M1 in newly synthesized palmitate molecules was calculated (column U), and this value was compared to EM1 (column M) to determine fractional de novo lipogenesis (column W). The values observed (12.8% fasted, 29.4% fed) are 5–10 times the value in normal men and demonstrate a substantial contribution of endogenous fat synthesis to his body fat pool. The turnover rate of his plasma VLDL-palmitate was also calculated from the decay curve of EM2 (column N) between time 1700 through 2400. Combining the fractional VLDL-palmitate synthesis rate with his absolute VLDL-palmitate turnover rate allows calculation of his absolute new fat sythesis rate, which was confirmed to be 5–10 fold elevated.

EXAMPLE 7 (½)

The following is an algorithm for calculating theoretical isotopomer abundances for a generic molecule made up of natural abundance atoms and/or enriched atoms. In order to generate isotopomer distributions for theoretical groups of atoms the Multinomial Expansion (equation 1) is used along with natural abundance values found in the literature.

$$p = \frac{N!}{\prod_{i=1}^{n} x_i!} \times \prod_{i=1}^{n} \Theta_i^{x_i} \quad \text{The Multinomial Expansion} \quad \text{Equation 1}$$

For example, in order to calculate the probability of an M$_3$ in a group of x Oxygen atoms (assume x≧3;p(M$_3$, O$_x$)) one must calculate the probability that the M$_3$ is due to the incorporation of 3$^{17}$O's and no $^{18}$O's or 1$^{17}$O and 1$^{18}$O:

$$p(M_3, O_x) = \frac{x!}{3!(x-3)!} \times (0.99759)^{(x-3)}(0.00037)^3 +$$

$$\frac{x!}{1!1!(x-2)!} \times (0.99759)^{(x-2)}(0.00037)(0.00204)$$

| | Natural Abundance Distributions for Atoms and some Theoretical Molecules (x = 2, y = 3, z = 8) | | | | | | |
|---|---|---|---|---|---|---|---|
| atom | $M_0$ | $M_1$ | $M_2$ ... | ... $M_x$ ... | ... $M_y$ ... | ... $M_{x+y}$ ... | ... $M_{(x+y)z}$ |
| $^{12,13}C$ | | — | — | — | — | — | |
| $^{1,2}H$ | | | — | — | — | — | |
| $^{15,17,18}O$ | | | — | — | — | — | — |
| $C_x$ | | | | — | | — | — |
| $H_y$ | | | | | — | — | — |
| $C_xH_y$ | | | | | | — | — |
| $(C_xH_y)_z$ | | | | | | | — |

For a theoretical molecule $C_xH_y$, natural abundances of isotopes are used to calculate theoretical distributions for x Carbons and y Hydrogens. The distributions are then used to calculate the theoretical distribution for $C_xH_y$. For example, the probability of an $M_2$ is calculated as follows:

$$p(M_2, C_xH_y) = (p(M_0, C_x) \times p(M_2, H_y)) + (p(M_1, H_y)) + (p(M_0, C_x) \times p(M_2, H_y)) \quad \text{equation 2}$$

or, more generally:

$$P(M_n, A_xB_y) = \sum_{i=0}^{n} p(M_i, A_x) \times p(M_{n-i}, B_y), \quad \text{equation 3}$$

where $0 \leq n \leq x+y$. and A and B can be either atomic or molecular distributions. In this way an entire distribution pattern for $C_xH_y$ can be calculated, from $M_0$ to $M_{x+y}$

| Example 7 (2/2) Distribution Calculation for $(^{NA}C_{x-1}*CH_y)_z$ (x = 2, y = 3, z = 8) | | | |
|---|---|---|---|
| atom group | $M_0$ | $M_1$ ... | ... $M_{(x+y)z}$ |
| $H_{yz}$ | | — | |
| $^{NA}C_{(x-1)z}$ | | — | |
| $(^{NA}C_{x-1}H_y)_z$ | | — | |
| $*C_z$ | | — | |
| $(^{NA}C_{x-1}*CH_y)_z$ | | — | |

Consider a theoretical molecule that is a polymer of $C_xH_y$ submits, i.e. $(C_xH_y)_z$. If one ¹carbon atom per $C_xH_y$ unit is enriched (*C) while all other atoms are natural abundance ($^{NA}C$), then there is a range of $(C_xH_y)_z$ isotopmers that can exist due to incorporated label $(^{NA}C_{x-1}*CH_y)$ from $M_0 \rightarrow M_z$. A table is generated for this molecule, treating the carbon positions that can be enriched as a separate pool of atoms as they will have a different distribution than that due to natural abundance. Using natural abundances and equation 1 we generate the $^{NA}C_{(x-1)z}$ and $^{NA}H_{yz}$ distributions. We then generate the $(^{NA}C_{x-1}^{NA}H_y)_z$ distribution using equation 3. Now, we vary the enrichment (p) of $*C_z$, the carbon atoms that can be enriched. For each p the distribution of subunits in $*C_z$ calculated. This subunit distribution is combined with the appropriate isotopomer distributions for the number of enriched (*C) and unenriched ($^{NA}C$) carbons in the pool of potentially enriched carbons. At this point, the two distributions (enriched and unenriched) are combined (equation 3) to give a single isotopomer distribution for $*C_z$. For each enrichment that the isotopomer distribution of $*C_z$ is calculated there is a distribution that can be generated for the entire polymer $(^{NA}C_{x-1}*CH_y)_z$ using equation 3 where $A = (^{NA}C_{x-1}H_y)_z$ and $B = *C_z$. This leads to a table as follows

| $(^{NA}C_{x-1}*CH_y)_z$ Distribution with varying precursor enrichment (p) (x = 2, y = 3, z = 8) | | | |
|---|---|---|---|
| p | $M_0$ | $M_1$ ... | ... $M_{(x+y)z}$ |
| 0.00 | | | |
| 0.01 | | | |
| 0.02 | | | |
| 0.03 | | | |
| 0.04 | | | |
| 0.05 | | | |

¹In the general case n atoms per subunit can be enriched. This changes the molecular formulas in the example to $(^{NA}C_{x-n}*CH_y)_z$ and $*C_{zn}$.

While the invention has been described with reference to specific methods and embodiments, it will be appreciated that various modifications and changes may be made without departing from the invention.

TABLE 1

ACETYL-CoA ENRICHMENT FROM ISOTOPOMERS AND XENOBIOTIC PROBE
Mass spectral data of VLDL fatty acids in human subjects and calculations of lipogenic hepatic acetyl-CoA enrichments by mass isotopomer method

| | Isotopomer Ratio Method | | | |
|---|---|---|---|---|
| Subject | $M_2/(M_0 + M_1 + M_2)$ | $M_1/(M_0 + M_1 + M_2)$ | $EM_2/EM_1$ | Calculated P, MPE |
| 1 Baseline | 0.0180 | 0.1613 | | |
| Enriched | 0.0211 | 0.1685 | 0.4306 | 4.60 |
| 2 Baseline | 0.0179 | 0.1603 | | |
| Enriched | 0.0227 | 0.1711 | 0.4444 | 4.84 |
| 3 Baseline (C-16) | 0.0181 | 0.1610 | | |
| Enriched (C-16) | 0.0234 | 0.1713 | 0.5088 | 5.26 |
| Baseline (C-18) | 0.0182 | 0.1750 | | |
| Enriched (C-18) | 0.0209 | 0.1806 | 0.5055 | 4.40 |
| 4 Baseline (C-16) | 0.0180 | 0.1600 | | |
| Enriched (C-16) | 0.0230 | 0.1716 | 0.4312 | 4.61 |
| Baseline (C-18) | 0.0210 | 0.1732 | | |
| Enriched (C-18) | 0.2039 | 0.1790 | 0.4988 | 4.50 |
| 5 Baseline | 0.0181 | 0.1609 | | |
| Enriched | 0.0257 | 0.1744 | 0.5298 | 6.49 |
| 6 Baseline | 0.0181 | 0.1609 | | |
| Enriched | 0.0252 | 0.1747 | 0.5119 | 6.01 |
| 7 Baseline (C-16) | 0.0184 | 0.1610 | | |

TABLE 1-continued

ACETYL-CoA ENRICHMENT FROM ISOTOPOMERS AND XENOBIOTIC PROBE
Mass spectral data of VLDL fatty acids in human subjects and calculations of
lipogenic hepatic acetyl-CoA enrichments by mass isotopomer method

| Subject | Isotopomer Ratio Method | | | Calculated P, MPE |
|---|---|---|---|---|
| | $M_2/(M_0 + M_1 + M_2)$ | $M_1/(M_0 + M_1 + M_2)$ | $EM_2/EM_1$ | |
| Enriched (C-16) | 0.0252 | 0.1781 | 0.3983 | 4.04 |
| Baseline (C-18) | 0.0213 | 0.1740 | | |
| Enriched (C-18) | 0.0242 | 0.1800 | 0.4833 | 4.28 |
| 8 Baseline | 0.0179 | 0.1596 | | |
| Enriched | 0.0228 | 0.1679 | 0.4704 | 5.29 |
| 9 Baseline | 0.0178 | 0.1596 | | |
| Enriched | 0.2097 | 0.1772 | 0.6775 | 8.88 |
| 10 Baseline | 0.0186 | 0.1629 | | |
| Enriched | 0.0244 | 0.1759 | 0.4445 | 4.84 |
| 11 Baseline | 0.0186 | 0.1629 | | |
| Enriched | 0.0283 | 0.1785 | 0.6218 | 7.91 |
| 12 Baseline | 0.0179 | 0.1598 | | |
| Enriched | 0.2013 | 0.1682 | 0.3953 | 3.99 |
| 13 Baseline | 0.0178 | 0.1599 | | |
| Enriched | 0.0241 | 0.1720 | 0.5212 | 6.17 |
| 14 Baseline | 0.0180 | 0.1597 | | |
| Enriched | 0.0271 | 0.1792 | 0.4664 | 5.22 |
| 15 Baseline | 0.0182 | 0.1621 | | |
| Enriched | 0.0257 | 0.1766 | 0.5171 | 6.10 |
| 16 Baseline | 0.0181 | 0.1595 | | |
| Enriched | 0.0257 | 0.1762 | 0.4560 | 5.04 |

Molecular anion ($M_0$) and enriched anions ($M_1$ and $M_2$) isotopomer frequencies were measured by gas chromatography-mass spectometry, as detailed in text. Baseline (unenriched) values were compared to average of 1–3 enriched values, to calculate excess $M_1$ and $M_2$ molar frequencies and their ratio ($EM_2/EM_1$). Calculated acetyl-CoA enrichments are from equations in APPENDIX FIG. 6. Very low-density lipoprotein (VLDL) stearate (C-18) ratios wer e used in those individuals whose $M_1$ excesses were >0.50 molar percent excess (MPR).

TABLE 2

| Refeeding protocol/subject no. | Measured p (SMX-Ac MPE) | Calculated EF[M + 1/(M + 0) + (M + 1)] | | Measured VLDL-FA enrichment (MPE) | | Percent de novo lipogenesis | |
|---|---|---|---|---|---|---|---|
| | | C-16 | C-18 | C-16 | C-18 | C-16 | C-18 |
| I. Ensure refed | | | | | | | |
| 1. Fasted | — | — | — | — | — | — | — |
| Early fed | 6.64 | 0.2842 | 0.2974 | 0.57 | 0.08 | 2.01 | 0.27 |
| Late fed | 7.60 | 0.3135 | 0.3270 | 0.60 | 0.06 | 1.91 | 0.18 |
| 2. Fasted | — | — | — | — | — | — | — |
| Early fed | 6.60 | 0.2830 | 0.2961 | 0.63 | 0.00 | 2.23 | 0.00 |
| Late fed | 6.21 | 0.2703 | 0.2833 | 1.08 | 0.00 | 3.99 | 0.00 |
| 3. Fasted | 7.19 | 0.3013 | 0.3147 | 0.16 | 0.19 | 0.53 | 0.60 |
| Early fed | 7.83 | 0.3202 | 0.3337 | 0.24 | 0.41 | 0.75 | 1.23 |
| Late fed | 7.78 | 0.3187 | 0.3323 | 0.42 | 0.61 | 1.32 | 1.84 |
| 4. Fasted | 6.36 | 0.2752 | 0.2883 | 0.50 | 0.17 | 1.82 | 0.59 |
| Early fed (10) | 7.97 | 0.3246 | 0.3377 | 0.38 | 0.17 | 1.17 | 0.50 |
| Late fed (10) | 8.34 | 0.3344 | 0.3480 | 0.38 | 0.32 | 1.14 | 0.92 |
| 5. Fasted | 7.20 | 0.3016 | 0.3150 | 0.03 | 0.04 | 0.10 | 0.13 |
| Early fed | 7.89 | 0.3219 | 0.3355 | 0.20 | 0.29 | 0.62 | 0.86 |
| Late fed | 8.24 | 0.3316 | 0.3453 | 0.33 | 0.26 | 1.00 | 0.75 |
| 6. Fasted | 3.66 | 0.1775 | 0.1883 | 0.14 | 0.02 | 0.79 | 0.11 |
| Early fed | 4.63 | 0.2149 | 0.2267 | 0.06 | 0.12 | 0.28 | 0.53 |
| Late fed | 4.70 | 0.2175 | 0.2293 | 0.15 | 0.11 | 0.69 | 0.48 |
| 7. Fasted | — | — | — | — | — | — | — |
| Early fed | 6.35 | — | — | — | — | — | — |
| Late fed | 6.27 | 0.2720 | 0.2849 | 0.39 | 0.08 | 1.43 | 0.28 |
| 8. Fasted | 5.57 | 0.2487 | 0.2613 | 0.17 | 0.08 | 0.68 | 0.31 |
| II. Breakfast refed | | | | | | | |
| 1. Fasted | 3.23 | 0.1602 | 0.1704 | 0.16 | 0.15 | 1.00 | 0.88 |
| Early fed | 5.34 | 0.2406 | 0.2530 | — | — | — | — |
| Late fed | 5.82 | 0.2573 | 0.2700 | — | — | — | — |
| 2. Fasted | 6.24 | 0.2713 | 0.2843 | 0.08 | 0.11 | 0.29 | 0.11 |
| Early fed | 5.72 | 0.2539 | 0.2665 | 0.09 | 0.00 | 0.35 | 0.00 |
| Late fed | 4.99 | 0.2281 | 0.2402 | 0.14 | 0.04 | 0.61 | 0.04 |
| 3. Fasted | 4.02 | 0.1917 | 0.2029 | 0.14 | 0.06 | 0.73 | 0.30 |
| Early fed | 4.69 | 0.2171 | 0.2289 | 0.43 | 0.23 | 1.98 | 1.00 |
| Late fed | 4.72 | 0.2182 | 0.2301 | 0.37 | 0.22 | 1.70 | 0.96 |
| 4. Fasted | 4.71 | 0.2179 | 0.2297 | 0.50 | 0.12 | 2.30 | 0.52 |
| Early fed | 4.72 | 0.2182 | 0.2301 | 0.92 | 0.25 | 4.22 | 1.09 |
| Late fed | 4.70 | 0.2175 | 0.2293 | 0.88 | 0.27 | 4.05 | 1.18 |
| 5. Fasted | — | — | — | — | — | — | — |
| Early fed | 3.94 | — | — | — | — | — | — |
| Late fed | 4.87 | 0.2241 | 0.2361 | 0.56 | 0.16 | 2.50 | 0.07 |
| 6. Fasted | — | — | — | — | — | — | — |
| Early fed | 5.37 | 0.2408 | 0.2533 | 0.05 | 0.00 | 0.21 | 0.00 |
| Late fed | 5.54 | 0.2476 | 0.2602 | 0.06 | 0.00 | 0.24 | 0.00 |

TABLE 2-continued

| Refeeding protocol/subject no. | Measured p (SMX-Ac MPE) | Calculated EF[M + 1/(M + 0) + (M + 1)] | | Measured VLDL-FA enrichment (MPE) | | Percent de novo lipogenesis | |
|---|---|---|---|---|---|---|---|
| | | C-16 | C-18 | C-16 | C-18 | C-16 | C-18 |
| 7. Fasted | 3.66 | 0.1775 | 0.1883 | 0.17 | 0.09 | 0.96 | 0.48 |
| Early fed | 4.98 | 0.2281 | 0.2402 | 0.40 | 0.12 | 1.75 | 0.50 |
| Late fed | 4.87 | 0.2240 | 0.2359 | 0.61 | 0.14 | 2.72 | 0.59 |
| III. Intravenous glucose refed | | | | | | | |
| 1. Fasted | — | — | — | — | — | — | — |
| Early fed | 4.30 | 0.2025 | 0.2139 | 0.23 | 0.19 | 0.14 | 0.89 |
| Late fed | 4.88 | 0.2241 | 0.2361 | 0.47 | 0.29 | 2.10 | 1.23 |
| 2. Fasted | — | — | — | — | — | — | — |
| Early fed | 5.68 | 0.2525 | 0.2651 | 0.29 | 0.18 | 1.15 | 0.68 |
| Late fed | 5.98 | 0.2627 | 0.2755 | 0.34 | 0.19 | 1.29 | 0.69 |
| 3. Fasted | 4.53 | 0.2112 | 0.2228 | 0.16 | 0.00 | 0.76 | 0.00 |
| Early fed (10) | 4.62 | 0.2145 | 0.2263 | 0.21 | 0.00 | 0.98 | 0.00 |
| Laate fed (10) | 4.42 | 0.2070 | 0.2186 | 0.35 | 0.00 | 1.69 | 0.00 |

TABLE 3

Calculation of precursor enrichments (p) from excess isotopomer ratios (R) in humans

| Subject (tracer) | Time | Enrichments (MPE) | | | | R | | | Calculated p (MPE) | | |
|---|---|---|---|---|---|---|---|---|---|---|---|
| | | $EM_1$ | $EM_2$ | $EM_3$ | $EM_4$ | $EM_1/EM_{1-4}$ | $EM_2/EM_{1-4}$ | $EM_3/EM_{1-4}$ | $EM_1/EM_{1-4}$ | $EM_2/EM_{1-4}$ | $EM_3/EM_{1-4}$ |
| #(1) | 0900 | 0.43 | 0.53 | 0.19 | 0.01 | 0.3757 | 0.4680 | 0.1643 | 5.33 | 11.21 | 5.38 |
| ($[2-^{13}C]$-Ac) | 1300 | 0.28 | 0.53 | 0.18 | 0.03 | 0.2716 | 0.5137 | 0.1747 | 7.34 | 20.59 | 5.78 |
| | 1700 | 0.35 | 0.61 | 0.21 | 0.03 | 0.2890 | 0.5103 | 0.1725 | 6.98 | 19.73 | 5.67 |
| #(2) | 0900 | 0.55 | 0.61 | 0.24 | 0.07 | 0.3746 | 0.4151 | 0.1635 | 5.35 | 5.22 | 5.35 |
| ($[2-^{13}C]$-Ac) | 1700 | 0.60 | 0.61 | 0.25 | 0.07 | 0.2910 | 0.4080 | 0.1629 | 5.06 | 4.26 | 5.33 |
| #(3) | 0830 | 0.18 | 0.23 | 0.08 | 0.01 | 0.3504 | 0.4564 | 0.1668 | 7.30 | 11.47 | 6.90 |
| ($[1-^{13}C]$-Ac) | 1100 | 0.19 | 0.28 | 0.10 | 0.02 | 0.3223 | 0.4746 | 0.1681 | 7.96 | 14.71 | 6.95 |
| | 1300 | 0.19 | 0.29 | 0.11 | 0.03 | 0.3078 | 0.4668 | 0.1810 | 8.31 | 13.23 | 7.53 |
| | 1500 | 0.35 | 0.42 | 0.15 | 0.06 | 0.2607 | 0.4309 | 0.1510 | 7.07 | 8.03 | 6.19 |
| | 1700 | 0.49 | 0.57 | 0.20 | 0.05 | 0.3692 | 0.4359 | 0.1533 | 6.87 | 8.62 | 6.29 |
| | 1800 | 0.49 | 0.60 | 0.20 | 0.05 | 0.3639 | 0.4459 | 0.1496 | 6.99 | 9.92 | 6.12 |
| #(4) | 0900 | 0.36 | 0.52 | 0.17 | 0.04 | 0.3302 | 0.4743 | 0.1578 | 6.17 | 12.24 | 5.14 |
| ($[2-^{13}C]$-Ac) | 1300 | 0.50 | 0.67 | 0.29 | 0.07 | 0.3293 | 0.4374 | 0.1877 | 6.19 | 7.21 | 6.22 |
| | 1700 | 0.60 | 0.88 | 0.35 | 0.10 | 0.3118 | 0.4574 | 0.1803 | 6.53 | 9.64 | 5.95 |
| #(5) | 0900 | 0.33 | 0.60 | 0.27 | 0.09 | 0.2547 | 0.4649 | 0.2100 | 7.69 | 10.72 | 7.03 |
| ($[2-^{13}C]$-Ac) | 1100 | 0.39 | 0.60 | 0.26 | 0.10 | 0.2892 | 0.4446 | 0.1941 | 6.98 | 8.02 | 6.45 |
| | 1300 | 0.36 | 0.58 | 0.27 | 0.09 | 0.2744 | 0.4463 | 0.2092 | 7.28 | 8.22 | 7.00 |
| | 1500 | 0.25 | 0.61 | 0.28 | 0.10 | 0.2040 | 0.4921 | 0.2248 | 8.80 | 15.58 | 7.57 |
| | 1700 | 0.45 | 0.63 | 0.29 | 0.10 | 0.3076 | 0.4241 | 0.1973 | 6.61 | 5.95 | 6.57 |

TABLE 4

Endogenous cholesterol synthesis in rats

| Group | RAT# | P (MPE) | $A_1$* (MPE) | $M_1$* (MPE) | f (%) |
|---|---|---|---|---|---|
| I) Control | B161 | 9.01 | 18.80 | 0.43 | 2.31 |
| | B163 | 9.22 | 18.66 | 0.35 | 1.89 |
| | B164 | 9.40 | 18.54 | 0.54 | 2.93 |
| | B165 | 8.19 | 19.28 | 0.82 | 4.23 |
| | B166 | 5.90 | 19.50 | 1.01 | 5.17 |
| | B167 | 6.20 | 19.61 | 0.67 | 3.40 |
| | 841 | 3.57 | 16.45 | 0.17 | 1.04 |
| | 845 | 4.56 | 18.29 | 0.21 | 1.14 |
| | 849 | 5.74 | 19.42 | 0.25 | 1.27 |
| | 844 | 8.76 | 13.78 | 0.55 | 3.99 |
| | 848 | 8.45 | 15.56 | 0.68 | 4.39 |
| Mean ± S.E.: | | | | | 2.89 ± .44 |
| II) TNF-treated | B342 | 5.54 | 19.30 | 02.29 | 8.43 |
| | B343 | 3.89 | 17.14 | 02.51 | 11.88 |
| | B344 | 4.32 | 17.92 | 02.38 | 14.65 |
| | B334 | 6.75 | 19.69 | 0.177 | 9.00 |
| | B335 | 5.70 | 19.40 | 02.58 | 13.32 |
| | B336 | 5.18 | 19.01 | 01.46 | 7.70 |
| | B337 | 5.67 | 19.38 | 02.95 | 15.24 |
| Mean ± S.E.: | | | | | 11.46 ± 1.17 |

TABLE 5A

| p | A* (1) | A* (2) | A* (3) | A* (4) | Ratio A* (1)/all | Ratio A* (2)/all | ratio A* (3)/all | ratio A* (4)/all |
|---|---|---|---|---|---|---|---|---|
| .000 | | | | | | | | |
| .001 | .00533 | .00108 | .00012 | .00001 | .81418 | .16556 | .01871 | .00155 |
| .002 | .01058 | .00220 | .00025 | .00002 | .81065 | .16847 | .10927 | .00161 |
| .003 | .01575 | .00334 | .00039 | .00003 | .80713 | .17136 | .01984 | .00167 |
| .004 | .02083 | .00452 | .00053 | .00004 | .80360 | .17423 | .02043 | .00174 |
| .005 | .02584 | .00572 | .00068 | .00006 | .80009 | .17709 | .02102 | .00180 |
| .006 | .03076 | .00695 | .00084 | .00007 | .79657 | .17993 | .02163 | .00187 |
| .007 | .03561 | .00820 | .00100 | .00009 | .79305 | .18275 | .02224 | .00195 |
| .008 | .04037 | .00949 | .00117 | .00010 | .78956 | .18555 | .02287 | .00202 |
| .009 | .04506 | .01080 | .00135 | .00012 | .78605 | .18834 | .02351 | .00210 |

TABLE 5A-continued

| p | A* (1) | A* (2) | A* (3) | A* (4) | Ratio A* (1)/all | Ratio A* (2)/all | ratio A* (3)/all | ratio A* (4)/all |
|---|---|---|---|---|---|---|---|---|
| .010 | .04967 | .01213 | .00153 | .00014 | .78256 | .19111 | .02416 | .00218 |
| .011 | .05420 | .01349 | .00173 | .00016 | .77906 | .19386 | .02482 | .00226 |
| .012 | .05866 | .01487 | .00193 | .00018 | .77557 | .19660 | .02549 | .00234 |
| .013 | .06304 | .01627 | .00214 | .00020 | .77209 | .19931 | .02617 | .00243 |
| .014 | .06735 | .01770 | .00235 | .00022 | .76860 | .20201 | .02686 | .00252 |
| .015 | .07159 | .01915 | .00258 | .00024 | .76513 | .20470 | .02757 | .00261 |
| .016 | .07575 | .02062 | .00281 | .00027 | .76165 | .20736 | .02828 | .00270 |
| .017 | .07984 | .02211 | .00305 | .00030 | .75818 | .21001 | .02900 | .00280 |
| .018 | .08385 | .02363 | .00330 | .00032 | .75472 | .21264 | .02974 | .00290 |
| .019 | .08780 | .02516 | .00356 | .00035 | .75126 | .21526 | .03048 | .00301 |
| .020 | .09168 | .02671 | .00383 | .00038 | .74780 | .21786 | .03123 | .00311 |
| .021 | .09549 | .02828 | .00410 | .00041 | .74435 | .22043 | .03200 | .00322 |
| .022 | .09923 | .02987 | .00439 | .00045 | .74090 | .22300 | .03277 | .00333 |
| .023 | .10290 | .03147 | .00468 | .00048 | .73746 | .22554 | .03356 | .00344 |
| .024 | .10650 | .03309 | .00498 | .00052 | .73402 | .22807 | .03435 | .00356 |
| .025 | .11004 | .03473 | .00529 | .00055 | .73058 | .23058 | .03515 | .00368 |
| .026 | .11351 | .03638 | .00561 | .00059 | .72715 | .23307 | .03597 | .00381 |
| .027 | .11691 | .03805 | .00594 | .00064 | .72373 | .23555 | .03679 | .00393 |
| .028 | .12025 | .03974 | .00628 | .00068 | .72031 | .23801 | .03762 | .00406 |
| .029 | .12353 | .04143 | .00663 | .00072 | .71689 | .24045 | .03847 | .00419 |
| .030 | .12674 | .04314 | .00698 | .00077 | .71348 | .24287 | .03932 | .00433 |
| .031 | .12989 | .04487 | .00735 | .00082 | .71007 | .24528 | .04018 | .00447 |
| .032 | .13298 | .04661 | .00772 | .00087 | .70667 | .24767 | .04105 | .00461 |
| .033 | .13601 | .04836 | .00811 | .00092 | .70327 | .25004 | .04193 | .00476 |
| .034 | .13897 | .05012 | .00850 | .00097 | .69988 | .25240 | .04282 | .00491 |
| .035 | .14188 | .05189 | .00891 | .00103 | .69649 | .25474 | .04371 | .00506 |
| .036 | .14473 | .05368 | .00932 | .00109 | .69310 | .25706 | .04462 | .00522 |
| .037 | .14751 | .05547 | .00974 | .00115 | .68973 | .25936 | .04554 | .00538 |
| .038 | .15024 | .05727 | .01017 | .00121 | .68635 | .26165 | .04646 | .00554 |
| .039 | .15291 | .05909 | .01061 | .00128 | .68298 | .26392 | .04739 | .00571 |
| .040 | .15552 | .06091 | .01106 | .00134 | .67962 | .26617 | .04834 | .00588 |
| .041 | .15808 | .06274 | .01152 | .00141 | .67626 | .26840 | .04929 | .00605 |
| .042 | .16058 | .06458 | .01199 | .00149 | .67291 | .27062 | .05025 | .00623 |
| .043 | .16303 | .06643 | .01247 | .00156 | .66956 | .27282 | .05121 | .00641 |
| .044 | .16542 | .06828 | .01296 | .00164 | .66621 | .27501 | .05219 | .00659 |
| .045 | .16775 | .07014 | .01346 | .00172 | .66287 | .27717 | .05317 | .00678 |
| .046 | .17004 | .07201 | .01396 | .00180 | .65954 | .27932 | .04317 | .00697 |
| .047 | .17227 | .07389 | .01448 | .00188 | .65621 | .28145 | .05517 | .00717 |
| .048 | .17444 | .07577 | .01501 | .00197 | .65289 | .28357 | .05617 | .00737 |
| .049 | .17657 | .07765 | .01555 | .00206 | .64957 | .28566 | .05719 | .00757 |
| .050 | .17864 | .07954 | .01609 | .00215 | .64626 | .28774 | .05821 | .00778 |
| .051 | .18066 | .08143 | .01665 | .00225 | .64295 | .28981 | .05925 | .00799 |
| .052 | .18264 | .08333 | .01721 | .00234 | .63965 | .29185 | .06029 | .00821 |
| .053 | .18456 | .08523 | .01779 | .00244 | .63635 | .29388 | .06133 | .00843 |
| .054 | .18643 | .08714 | .01837 | .00255 | .63306 | .29590 | .06239 | .00865 |
| .055 | .18826 | .08905 | .01897 | .00265 | .62977 | .29789 | .06345 | .00888 |
| .056 | .19003 | .09096 | .01957 | .00276 | .62649 | .29987 | .06452 | .00911 |
| .057 | .19176 | .09287 | .02018 | .00288 | .62322 | .30183 | .06560 | .00935 |
| .058 | .19344 | .09479 | .02081 | .00299 | .61995 | .30378 | .06668 | .00959 |
| .059 | .19508 | .09670 | .02144 | .00311 | .61669 | .30570 | .06778 | .00984 |
| .060 | .19667 | .09862 | .02208 | .00323 | .61343 | .30761 | .06887 | .01008 |
| .061 | .19821 | .10054 | .02273 | .00336 | .61017 | .30951 | .06998 | .01034 |
| .062 | .19971 | .10246 | .02339 | .00349 | .60693 | .31138 | .07109 | .01060 |
| .063 | .20117 | .10438 | .02406 | .00362 | .60369 | .31324 | .07221 | .01086 |
| .064 | .20258 | .10630 | .02474 | .00375 | .60045 | .31509 | .07334 | .01112 |
| .065 | .20394 | .10822 | .02543 | .00389 | .59722 | .31691 | .07447 | .01139 |
| .066 | .20527 | .11014 | .02613 | .00403 | .59400 | .31872 | .07561 | .01167 |
| .067 | .20655 | .11206 | .02684 | .00418 | .59078 | .32051 | .07676 | .01195 |
| .068 | .20779 | .11398 | .02755 | .00433 | .58756 | .32229 | .07791 | .01223 |
| .069 | .20899 | .11589 | .02828 | .00448 | .58436 | .32405 | .07907 | .01252 |
| .070 | .21014 | .11781 | .02901 | .00463 | .58116 | .32579 | .08024 | .01282 |
| .071 | .21126 | .11972 | .02976 | .00479 | .57796 | .32752 | .08141 | .01311 |
| .072 | .21234 | .12163 | .03051 | .00496 | .57477 | .32923 | .08259 | .01342 |
| .073 | .21337 | .12353 | .03127 | .00512 | .57159 | .33092 | .08377 | .01372 |
| .074 | .21437 | .12544 | .03204 | .00529 | .56841 | .33259 | .08496 | .01403 |
| .075 | .21533 | .12734 | .03282 | .00547 | .56524 | .33425 | .08616 | .01435 |
| .076 | .21625 | .12923 | .03361 | .00564 | .56207 | .33589 | .08736 | .01467 |
| .077 | .21714 | .13113 | .03441 | .00583 | .55891 | .33752 | .00857 | .01500 |
| .078 | .21198 | .13301 | .03521 | .00601 | .55576 | .33913 | .08978 | .01533 |
| .079 | .21879 | .13490 | .03603 | .00620 | .55261 | .34072 | .09100 | .01566 |
| .080 | .29156 | .13678 | .03685 | .00639 | .54947 | .34230 | .09222 | .01600 |
| .081 | .22030 | .13865 | .03768 | .00659 | .54634 | .34386 | .09345 | .01635 |
| .082 | .22100 | .14053 | .03852 | .00679 | .54321 | .34540 | .98469 | .01670 |
| .083 | .22167 | .14239 | .03937 | .00700 | .54009 | .34693 | .09593 | .01705 |
| .084 | .22230 | .14425 | .04023 | .00721 | .53697 | .34844 | .09718 | .01741 |
| .085 | .22290 | .14611 | .04110 | .00742 | .53386 | .34993 | .09843 | .01778 |
| .086 | .22346 | .15795 | .04197 | .00764 | .53076 | .35141 | .09968 | .01815 |
| .087 | .22399 | .14980 | .04285 | .00786 | .52766 | .35287 | .10094 | .01852 |
| .088 | .22449 | .15163 | .04374 | .00809 | .52457 | .35432 | .10221 | .01890 |
| .089 | .22496 | .15346 | .04464 | .00832 | .52149 | .35575 | .10348 | .01928 |

TABLE 5A-continued

| p | A* (1) | A* (2) | A* (3) | A* (4) | Ratio A* (1)/all | Ratio A* (2)/all | ratio A* (3)/all | ratio A* (4)/all |
|---|--------|--------|--------|--------|------------------|------------------|------------------|------------------|
| .090 | .25539 | .15528 | .04554 | .00855 | .51841 | .35716 | .10475 | .01967 |
| .091 | .22579 | .15710 | .04646 | .00879 | .51534 | .35856 | .10603 | .02007 |
| .092 | .22616 | .15891 | .04738 | .00904 | .51228 | .35994 | .10732 | .02047 |
| .093 | .22650 | .16071 | .04831 | .00928 | .50922 | .36130 | .10861 | .02087 |
| .094 | .22681 | .16250 | .04925 | .00954 | .50617 | .36265 | .10990 | .02128 |
| .095 | .22709 | .16429 | .05019 | .00979 | .50312 | .35398 | .11120 | .02170 |
| .096 | .22734 | .16607 | .05114 | .01005 | .50007 | .36530 | .11250 | .02212 |
| .097 | .22756 | .16784 | .05210 | .01032 | .49705 | .36660 | .11381 | .02254 |
| .098 | .22775 | .16960 | .05307 | .01059 | .49403 | .36789 | .11512 | .00297 |
| .099 | .22792 | .17136 | .05404 | .01087 | .49101 | .36916 | .11643 | .02341 |
| .100 | .22805 | .17310 | .05503 | .01115 | .48799 | .37041 | .11775 | .02385 |
| .101 | .22816 | .17484 | .05601 | .01143 | .48499 | .37165 | .11907 | .02430 |
| .102 | .22824 | .17656 | .05701 | .01172 | .48199 | .37287 | .12039 | .02475 |
| .103 | .22829 | .17828 | .05801 | .01201 | .47900 | .37407 | .12172 | .02520 |
| .104 | .22832 | .17999 | .05902 | .01231 | .47601 | .37526 | .12306 | .02567 |
| .105 | .22832 | .18169 | .06004 | .01261 | .47304 | .37644 | .12439 | .02613 |
| .106 | .22829 | .18338 | .06106 | .01292 | .47007 | .37760 | .12573 | .02661 |
| .107 | .22824 | .18506 | .06209 | .01323 | .46710 | .37874 | .12707 | .02708 |
| .108 | .22816 | .18674 | .06313 | .01355 | .46414 | .37987 | .12842 | .02757 |
| .109 | .22806 | .18840 | .06417 | .01387 | .46119 | .38098 | .12977 | .02806 |
| .110 | .22794 | .19005 | .06522 | .01420 | .45825 | .38208 | .13112 | .02855 |
| .111 | .22779 | .19169 | .06628 | .01453 | .45531 | .38316 | .13248 | .02905 |
| .112 | .22761 | .19332 | .06734 | .01487 | .45238 | .38422 | .13384 | .02955 |
| .113 | .22742 | .19494 | .06841 | .01521 | .44946 | .38527 | .13520 | .03006 |
| .114 | .22720 | .19655 | .06948 | .01556 | .44655 | .38631 | .13656 | .03058 |
| .115 | .22695 | .19815 | .07056 | .01591 | .44364 | .38733 | .13793 | .03110 |
| .116 | .22669 | .19974 | .07165 | .01627 | .44074 | .38834 | .13930 | .03163 |
| .117 | .22640 | .20131 | .07274 | .01663 | .43784 | .38933 | .14067 | .03216 |
| .118 | .22609 | .20288 | .07384 | .01700 | .43495 | .39030 | .14205 | .03270 |
| .119 | .22576 | .20444 | .07494 | .01737 | .43207 | .39126 | .14342 | .03324 |
| .120 | .22541 | .20598 | .07605 | .01775 | .42920 | .39220 | .14480 | .03379 |
| .121 | .22504 | .20751 | .07716 | .01813 | .42634 | .39313 | .14619 | .03435 |
| .122 | .22465 | .20903 | .07828 | .01852 | .04328 | .39405 | .14757 | .03491 |
| .123 | .22423 | .21054 | .07941 | .01891 | .42063 | .39495 | .14896 | .03547 |
| .124 | .22380 | .21204 | .08054 | .01931 | .41778 | .39583 | .15034 | .03604 |
| .125 | .22335 | .21353 | .08167 | .01971 | .41494 | .39670 | .15173 | .03662 |
| .126 | .22288 | .21500 | .08281 | .02012 | .41212 | .39756 | .15313 | .03720 |
| .127 | .22239 | .21647 | .08396 | .02053 | .40929 | .39840 | .15452 | .03779 |
| .128 | .22188 | .21792 | .08511 | .02095 | .40648 | .39922 | .15591 | .03838 |
| .129 | .22135 | .29136 | .08626 | .02138 | .40367 | .40004 | .15731 | .03898 |
| .130 | .22080 | .22078 | .08742 | .02180 | .40087 | .40083 | .15871 | .03959 |
| .131 | .22024 | .22220 | .08858 | .02224 | .09808 | .40152 | .16011 | .04020 |
| .132 | .21966 | .22360 | .08975 | .02268 | .39529 | .40238 | .16151 | .04081 |
| .133 | .21906 | .22499 | .09092 | .02312 | .39251 | .40314 | .16292 | .04143 |
| .134 | .21845 | .22637 | .09210 | .02357 | .38974 | .40388 | .16432 | .04206 |
| .135 | .21782 | .22773 | .09328 | .02403 | .38698 | .40460 | .16573 | .04269 |
| .136 | .21717 | .22909 | .09447 | .02449 | .38422 | .40531 | .16713 | .04333 |
| .137 | .21651 | .23043 | .09565 | .02496 | .38148 | .40601 | .16854 | .04398 |
| .138 | .21583 | .23176 | .09685 | .02543 | .37874 | .40669 | .16995 | .04453 |
| .139 | .21513 | .23307 | .09804 | .02591 | .37600 | .40736 | .17136 | .04528 |
| .140 | .21442 | .23437 | .00924 | .02639 | .37328 | .40801 | .17277 | .04594 |
| .141 | .21370 | .23566 | .10045 | .02688 | .37056 | .40865 | .17418 | .04661 |
| .142 | .21296 | .23694 | .10165 | .02737 | .36785 | .40928 | .17559 | .04728 |
| .143 | .21220 | .23820 | .10286 | .02787 | .36515 | .40989 | .17700 | .04796 |
| .144 | .21143 | .23945 | .10408 | .02838 | .36245 | .41049 | .17842 | .04865 |
| .145 | .21065 | .24069 | .10530 | .02889 | .35976 | .41107 | .17983 | .04934 |
| .146 | .20985 | .24192 | .10652 | .02940 | .35708 | .41164 | .18125 | .05003 |
| .147 | .20904 | .24313 | .10774 | .02992 | .35441 | .41220 | .18266 | .05073 |
| .148 | .20822 | .24433 | .10897 | .03045 | .35174 | .41274 | .18407 | .05144 |
| .149 | .20738 | .24552 | .11020 | .03098 | .34909 | .41327 | .18549 | .05215 |
| .150 | .20654 | .24669 | .11143 | .03152 | .34644 | .41379 | .18690 | .05287 |
| .151 | .20568 | .24785 | .11266 | .03206 | .34380 | .41429 | .18832 | .05359 |
| .152 | .20480 | .24899 | .11390 | .03261 | .34116 | .41478 | .18973 | .05432 |
| .153 | .20392 | .25013 | .11514 | .03317 | .33854 | .41525 | .19115 | .05506 |
| .154 | .20302 | .25125 | .11638 | .03372 | .33592 | .41572 | .19256 | .05580 |
| .155 | .20211 | .25236 | .11763 | .03429 | .33331 | .41617 | .19398 | .05655 |
| .156 | .20119 | .25345 | .11887 | .03486 | .33070 | .41660 | .19539 | .05730 |
| .157 | .20026 | .25453 | .12012 | .03544 | .32811 | .41703 | .19681 | .05806 |
| .158 | .19932 | .25560 | .12137 | .03602 | .32552 | .41744 | .19822 | .05882 |
| .159 | .19836 | .25665 | .12262 | .03660 | .32294 | .41783 | .19963 | .05959 |
| .160 | .19740 | .25769 | .12388 | .03720 | .32037 | .41822 | .20105 | .06037 |
| .161 | .19643 | .25872 | .12514 | .03780 | .31780 | .41859 | .20246 | .06115 |
| .162 | .19544 | .25973 | .12639 | .03840 | .31525 | .41894 | .20387 | .06194 |
| .163 | .19445 | .26073 | .12765 | .03901 | .31270 | .41929 | .20528 | .06273 |
| .164 | .19345 | .26172 | .12891 | .03962 | .31016 | .41962 | .20669 | .06353 |
| .165 | .19244 | .26270 | .13018 | .04024 | .30763 | .41994 | .20810 | .06433 |
| .166 | .19142 | .26366 | .13144 | .04087 | .30510 | .42025 | .20951 | .06514 |
| .167 | .19039 | .26460 | .13271 | .04150 | .30258 | .42054 | .21091 | .06596 |
| .168 | .18935 | .26554 | .13397 | .04214 | .30008 | .42083 | .21232 | .06678 |
| .169 | .18830 | .26646 | .13524 | .04278 | .29757 | .42110 | .21372 | .06761 |

TABLE 5A-continued

| p | A* (1) | A* (2) | A* (3) | A* (4) | Ratio A* (1)/all | Ratio A* (2)/all | ratio A* (3)/all | ratio A* (4)/all |
|---|---|---|---|---|---|---|---|---|
| .170 | .18724 | .26737 | .13651 | .04343 | .29508 | .42135 | .21513 | .06844 |
| .171 | .18618 | .26826 | .13778 | .04408 | .29260 | .42160 | .21653 | .06928 |
| .172 | .18511 | .26914 | .13905 | .04474 | .29012 | .42183 | .21793 | .07012 |
| .173 | .18403 | .27001 | .14032 | .04540 | .28765 | .42205 | .21933 | .07097 |
| .174 | .18294 | .27087 | .14159 | .04607 | .28519 | .42226 | .22073 | .07183 |
| .175 | .18184 | .27171 | .14286 | .04675 | .28273 | .42245 | .22212 | .07269 |
| .176 | .18074 | .27253 | .14413 | .04743 | .28029 | .42264 | .22352 | .07356 |
| .177 | .17963 | .27335 | .14541 | .04812 | .27785 | .42281 | .22491 | .07443 |
| .178 | .17852 | .27415 | .14668 | .04881 | .27542 | .42297 | .22630 | .07531 |
| .179 | .17739 | .27494 | .14795 | .04951 | .27300 | .42312 | .22769 | .97619 |
| .180 | .17626 | .27571 | .14923 | .05021 | .27059 | .42325 | .22908 | .07708 |
| .181 | .17513 | .27648 | .15050 | .05092 | .26818 | .42338 | .23047 | .07797 |
| .182 | .17399 | .27723 | .15177 | .05163 | .26578 | .42349 | .23185 | .07887 |
| .183 | .17284 | .27796 | .15305 | .05235 | .26339 | .42359 | .23323 | .07978 |
| .184 | .17168 | .27868 | .15432 | .05308 | .26101 | .42368 | .23461 | .08069 |
| .185 | .17053 | .27939 | .15559 | .05381 | .25864 | .42376 | .23599 | .08161 |
| .186 | .16936 | .28009 | .15686 | .05454 | .25627 | .42383 | .23736 | .08253 |
| .187 | .16819 | .28078 | .15814 | .05528 | .25392 | .42388 | .23874 | .08346 |
| .188 | .16701 | .28145 | .15941 | .05603 | .25157 | .42393 | .24011 | .08440 |
| .189 | .16583 | .28210 | .16068 | .05678 | .24922 | .42396 | .24148 | .08534 |
| .190 | .16465 | .28275 | .16195 | .05754 | .24689 | .42398 | .24284 | .08628 |
| .191 | .16346 | .28338 | .16322 | .05830 | .24457 | .42399 | .24421 | .08723 |
| .192 | .16226 | .28400 | .16449 | .05907 | .24225 | .42399 | .24557 | .08819 |
| .193 | .16106 | .28461 | .16576 | .05984 | .23994 | .42398 | .24693 | .08915 |
| .194 | .15986 | .28520 | .16702 | .06062 | .23764 | .42396 | .24828 | .09012 |
| .195 | .15865 | .28578 | .16829 | .06141 | .23534 | .42393 | .24964 | .09109 |
| .196 | .15744 | .28635 | .16955 | .06220 | .23306 | .42388 | .25099 | .09207 |
| .197 | .15623 | .28691 | .17082 | .06299 | .23078 | .42383 | .25234 | .09305 |
| .198 | .15501 | .28745 | .17208 | .06379 | .22851 | .42376 | .25368 | .09404 |
| .199 | .15378 | .28798 | .17334 | .06460 | .22625 | .42369 | .25502 | .09504 |
| .200 | .15256 | .28850 | .17460 | .06541 | .22400 | .42360 | .25636 | .09604 |
| .201 | .15133 | .28901 | .17586 | .06622 | .22175 | .42350 | .25770 | .09704 |
| .202 | .15010 | .28950 | .17711 | .06704 | .21952 | .42340 | .25903 | .09805 |
| .203 | .14886 | .28998 | .17837 | .06787 | .21729 | .42328 | .26036 | .09907 |
| .204 | .14762 | .29045 | .17962 | .06870 | .21507 | .42315 | .26169 | .10009 |
| .205 | .14638 | .29090 | .18087 | .06954 | .21286 | .42301 | .26301 | .10112 |
| .206 | .14514 | .29135 | .18212 | .07038 | .21065 | .42286 | .26433 | .10215 |
| .207 | .14389 | .29178 | .18337 | .07123 | .20846 | .42271 | .26565 | .10319 |
| .208 | .14264 | .29220 | .18461 | .07208 | .20627 | .42254 | .26696 | .10423 |
| .209 | .14139 | .29261 | .18586 | .07294 | .20409 | .42236 | .26827 | .10528 |
| .210 | .14014 | .29300 | .18710 | .07380 | .20191 | .42217 | .26958 | .10634 |
| .211 | .13888 | .29339 | .18834 | .07467 | .19975 | .42197 | .27088 | .10740 |
| .212 | .13763 | .29376 | .18958 | .07554 | .19759 | .42176 | .27218 | .10846 |
| .213 | .13637 | .29412 | .19081 | .07642 | .19545 | .42155 | .27348 | .10953 |
| .214 | .13511 | .29447 | .19204 | .07730 | .19331 | .42132 | .27477 | .11060 |
| .215 | .13384 | .29480 | .19327 | .07819 | .19117 | .42108 | .27606 | .11168 |
| .216 | .13258 | .29513 | .19450 | .07908 | .18905 | .42083 | .27735 | .11277 |
| .217 | .13131 | .29544 | .19572 | .07998 | .18694 | .42058 | .27863 | .11386 |
| .218 | .13005 | .29574 | .19695 | .08089 | .18483 | .42031 | .27990 | .14496 |
| .219 | .12878 | .29603 | .19817 | .08179 | .18273 | .42004 | .28118 | .11606 |
| .220 | .12751 | .29631 | .19938 | .08271 | .18064 | .41975 | .28245 | .11716 |
| .221 | .12624 | .29657 | .20060 | .08363 | .17855 | .41946 | .28371 | .11828 |
| .222 | .12497 | .29683 | .20181 | .08455 | .17648 | .41916 | .28497 | .11939 |
| .223 | .12370 | .29707 | .20302 | .08548 | .17441 | .41885 | .28623 | .12051 |
| .224 | .12243 | .29731 | .20422 | .08641 | .17235 | .41852 | .28748 | .12164 |
| .225 | .12116 | .29753 | .20542 | .08735 | .17030 | .41819 | .28873 | .12277 |
| .226 | .11989 | .29774 | .20662 | .08829 | .16826 | .41786 | 2.8998 | .12391 |
| .227 | .11862 | .29794 | .20782 | .08924 | .16622 | .41751 | .29122 | .12505 |
| .228 | .17734 | .29813 | .20901 | .09019 | .16419 | .41715 | .29246 | .12620 |
| .229 | .11607 | .29830 | .21020 | .09115 | .16217 | .41679 | .29369 | .12735 |
| .230 | .11480 | .29847 | .21138 | .09211 | .16016 | .41641 | .29492 | .12851 |
| .231 | .11352 | .29862 | .21257 | .09307 | .15816 | .41603 | .29614 | .12967 |
| .232 | .11225 | .29877 | .21375 | .09405 | .15616 | .41564 | .29736 | .13083 |
| .233 | .11098 | .29890 | .21492 | .09502 | .15418 | .41524 | .29857 | .13201 |
| .234 | .10971 | .29903 | .21609 | .09600 | .15220 | .41484 | .29978 | .13318 |
| .235 | .10844 | .29914 | .21726 | .09699 | .15023 | .41442 | .30099 | .13436 |
| .236 | .10716 | .29924 | .21843 | .09798 | .14826 | .41400 | .30219 | .13555 |
| .237 | .10589 | .29933 | .21959 | .09897 | .14631 | .41356 | .30339 | .13674 |
| .238 | .10462 | .29941 | .22074 | .09997 | .14436 | .41312 | .30458 | .13794 |
| .239 | .10335 | .29948 | .22190 | .10097 | .14242 | .41268 | .30577 | .13914 |
| .240 | .10209 | .29954 | .22305 | .10198 | .14049 | .41222 | .30695 | .14034 |
| .241 | .10082 | .29959 | .22419 | .10300 | .13856 | .41175 | .30813 | .14156 |
| .242 | .09955 | .29963 | .22534 | .10401 | .13665 | .41128 | .30930 | .14277 |
| .243 | .09829 | .29966 | .22647 | .10504 | .13474 | .41080 | .31047 | .14399 |
| .244 | .09702 | .29968 | .22761 | .10606 | .13284 | .41032 | .31163 | .14522 |
| .245 | .09576 | .29969 | .22874 | .10709 | .13095 | .40982 | .31279 | .14644 |
| .246 | .09450 | .29969 | .22986 | .10813 | .12906 | .40932 | .31394 | .14768 |
| .247 | .09324 | .29968 | .23098 | .10917 | .12719 | .40881 | .31509 | .14892 |
| .248 | .09198 | .29966 | .23210 | .11021 | .12532 | .40829 | .31623 | .15016 |
| .249 | .09072 | .29964 | .23321 | .11126 | .12346 | .40776 | .31737 | .15141 |

TABLE 5A-continued

| p | A* (1) | A* (2) | A* (3) | A* (4) | Ratio A* (1)/all | Ratio A* (2)/all | ratio A* (3)/all | ratio A* (4)/all |
|---|--------|--------|--------|--------|------------------|------------------|------------------|------------------|
| .250 | .08946 | .29960 | .23432 | .11231 | .12160 | .40723 | .31850 | .15266 |

TABLE 5B

Cholesterol Derived from 2-13C acetate

| p | A* (1) | A* (2) | A* (3) | A* (4) | Ratio A* (2)/all | Ratio A* (3)/all | ratio A* (4)/all |
|---|--------|--------|--------|--------|------------------|------------------|------------------|
| .000 | | | | | | | |
| .001 | .00778 | .00286 | .00044 | .00004 | .25714 | .03947 | .00377 |
| .002 | .01530 | .00579 | .00091 | .00009 | .26216 | .04128 | .00404 |
| .003 | .02255 | .00879 | .00142 | .00014 | .26710 | .04312 | .00433 |
| .004 | .02955 | .01185 | .00196 | .00020 | .27196 | .04501 | .00463 |
| .005 | .03630 | .01496 | .00254 | .00027 | .27675 | .04693 | .00495 |
| .006 | .04280 | .01813 | .00315 | .00034 | .28145 | .04889 | .00528 |
| .007 | .04906 | .02135 | .00380 | .00042 | .28608 | .05088 | .00563 |
| .008 | .05509 | .02462 | .00448 | .00051 | .29063 | .05290 | .00599 |
| .009 | .06089 | .02792 | .00520 | .00060 | .29511 | .05496 | .00638 |
| .010 | .06647 | .03127 | .00596 | .00071 | .29950 | .05706 | .00677 |
| .011 | .07183 | .03465 | .00675 | .00082 | .30382 | .05918 | .00719 |
| .012 | .07697 | .03806 | .00758 | .00094 | .03807 | .06133 | .00762 |
| .013 | .08190 | .04150 | .00844 | .00107 | .31223 | .06352 | .00807 |
| .014 | .08662 | .04497 | .00934 | .00121 | .31633 | .06573 | .00854 |
| .015 | .09115 | .04845 | .01028 | .00137 | .32035 | .06798 | .00903 |
| .016 | .09548 | .05196 | .01126 | .00153 | .32429 | .07025 | .00953 |
| .017 | .09962 | .05548 | .01226 | .00170 | .32816 | .07254 | .01006 |
| .018 | .10357 | .05901 | .01331 | .00188 | .33196 | .07487 | .01060 |
| .019 | .10733 | .06256 | .01439 | .00208 | .33569 | .07722 | .01116 |
| .020 | .11092 | .06611 | .01551 | .00229 | .33934 | .07959 | .01174 |
| .021 | .11433 | .06967 | .01666 | .00251 | .34292 | .08199 | .01234 |
| .022 | .11758 | .07323 | .01784 | .00274 | .34643 | .08441 | .01296 |
| .023 | .12065 | .07679 | .01906 | .00298 | .34987 | .08685 | .01359 |
| .024 | .12356 | .08035 | .02032 | .00324 | .35323 | .08931 | .01425 |
| .025 | .12632 | .08391 | .02160 | .00351 | .35653 | .09179 | .01493 |
| .026 | .12892 | .08745 | .02292 | .00380 | .35976 | .09430 | .01562 |
| .027 | .13136 | .09099 | .02428 | .00410 | .36292 | .09682 | .01634 |
| .028 | .13366 | .09452 | .02566 | .00441 | .36601 | .09936 | .01708 |
| .029 | .13582 | .09804 | .02708 | .00474 | .36903 | .10192 | .01784 |
| .030 | .13783 | .10154 | .02852 | .00508 | .37198 | .10449 | .01861 |
| .031 | .13971 | .10503 | .03000 | .00544 | .37487 | .10708 | .01941 |
| .032 | .14145 | .10850 | .03151 | .00581 | .37769 | .10969 | .02023 |
| .033 | .14307 | .11195 | .03305 | .00620 | .38044 | .11231 | .02107 |
| .034 | .14455 | .11538 | .03462 | .00660 | .38313 | .11494 | .02193 |
| .035 | .14592 | .11879 | .03621 | .00702 | .38576 | .11759 | .02281 |
| .036 | .14716 | .12217 | .03783 | .00746 | .38832 | .12025 | .02371 |
| .037 | .14828 | .12553 | .03948 | .00791 | .39081 | .12292 | .02463 |
| .038 | .14929 | .12887 | .04116 | .00838 | .39324 | .12560 | .02557 |
| .039 | .15019 | .13217 | .04286 | .00887 | .39561 | .12830 | .02654 |
| .040 | .15098 | .13545 | .04459 | .00937 | .39792 | .13100 | .02752 |
| .041 | .15167 | .13869 | .04634 | .00989 | .40016 | .13371 | .02853 |
| .042 | .15225 | .14191 | .04812 | .01042 | .40235 | .13643 | .02955 |
| .043 | .15273 | .14509 | .04992 | .01098 | .40447 | .13916 | .03060 |
| .044 | .15312 | .14824 | .05174 | .01155 | .40653 | .14190 | .03167 |
| .045 | .15341 | .15136 | .05359 | .01214 | .40854 | .14464 | .03276 |
| .046 | .15360 | .15444 | .05545 | .01274 | .41048 | .14739 | .03387 |
| .047 | .15371 | .15748 | .05734 | .01337 | .41236 | .15014 | .03500 |
| .048 | .15374 | .16049 | .05924 | .01401 | .41419 | .15290 | .03615 |
| .049 | .15368 | .16346 | .06117 | .01467 | .41596 | .15566 | .03732 |
| .050 | .15353 | .16640 | .06311 | .01534 | .41767 | .15843 | .03851 |
| .051 | .15331 | .16929 | .06508 | .01605 | .41933 | .16119 | .03973 |
| .052 | .15301 | .17215 | .06706 | .01675 | .42093 | .16397 | .04096 |
| .053 | .15264 | .17496 | .06905 | .01748 | .42248 | .16674 | .04222 |
| .054 | .15219 | .17774 | .07106 | .01823 | .42397 | .16951 | .04350 |
| .055 | .15167 | .18048 | .07309 | .01900 | .42541 | .17229 | .04479 |
| .056 | .15109 | .18317 | .07513 | .01979 | .42679 | .17506 | .04611 |
| .057 | .15044 | .18582 | .07719 | .02059 | .42812 | .17784 | .04745 |
| .058 | .14972 | .18843 | .07926 | .02142 | .42940 | .18061 | .04881 |
| .059 | .14895 | .19100 | .08134 | .02226 | .43062 | .18339 | .05018 |
| .060 | .14811 | .19353 | .08343 | .02312 | .43180 | .18616 | .05158 |
| .061 | .14722 | .19601 | .08554 | .02400 | .43292 | .18892 | .05300 |
| .062 | .14627 | .19845 | .08765 | .02489 | .43400 | .19169 | .05444 |
| .063 | .14526 | .20085 | .08978 | .02581 | .43502 | .19445 | .05590 |
| .064 | .14420 | .20320 | .09191 | .02674 | .43600 | .19721 | .05738 |
| .065 | .14310 | .20551 | .09406 | .02769 | .43693 | .19997 | .05888 |
| .066 | .14194 | .20778 | .09621 | .02866 | .43781 | .20272 | .06039 |
| .067 | .14074 | .21000 | .09836 | .02965 | .43864 | .20546 | .06193 |
| .068 | .13949 | .21218 | .10053 | .03066 | .43943 | .20820 | .06349 |
| .069 | .13820 | .21431 | .10270 | .03168 | .44017 | .21093 | .06506 |
| .070 | .13686 | .21640 | .10488 | .03272 | .44086 | .21366 | .06666 |

TABLE 5B-continued

Cholesterol Derived from 2-13C acetate

| p | A* (1) | A* (2) | A* (3) | A* (4) | Ratio A* (2)/all | Ratio A* (3)/all | ratio A* (4)/all |
|---|---|---|---|---|---|---|---|
| .071 | .13549 | .21845 | .10706 | .03378 | .44151 | .21638 | .06827 |
| .072 | .13408 | .22045 | .10925 | .03486 | .44211 | .29109 | .06991 |
| .073 | .13263 | .22241 | .11144 | .03595 | .44268 | .22179 | .07156 |
| .074 | .13114 | .22433 | .11363 | .03706 | .44319 | .22449 | .07323 |
| .075 | .12962 | .22620 | .11582 | .03819 | .44367 | .22718 | .07492 |
| .076 | .12806 | .22802 | .11802 | .03934 | .44410 | .22986 | .07662 |
| .077 | .12648 | .22981 | .12022 | .04051 | .44449 | .23253 | .07835 |
| .078 | .12486 | .23155 | .12242 | .04169 | .44484 | .23519 | .08009 |
| .079 | .12321 | .23325 | .12462 | .04289 | .44515 | .23784 | .08185 |
| .080 | .12154 | .23490 | .12682 | .04410 | .44542 | .24048 | .08363 |
| .081 | .11984 | .23651 | .12902 | .04534 | .44565 | .24311 | .08543 |
| .082 | .11811 | .23808 | .13122 | .04659 | .44584 | .24573 | .08724 |
| .083 | .11636 | .23961 | .13342 | .04785 | .44599 | .24834 | .08907 |
| .084 | .11459 | .24109 | .13561 | .04914 | .44611 | .25094 | .09092 |
| .085 | .11280 | .24253 | .13781 | .05043 | .44619 | .25352 | .09278 |
| .086 | .11098 | .24393 | .14000 | .05175 | .44623 | .25609 | .09466 |
| .087 | .10914 | .24529 | .14218 | .05308 | .44623 | .25866 | .09656 |
| .088 | .10729 | .24661 | .14437 | .05443 | .44620 | .26120 | .09848 |
| .089 | .10542 | .24789 | .14654 | .05579 | .44613 | .26374 | .10041 |
| .090 | .10353 | .24913 | .14872 | .05717 | .44603 | .26626 | .10235 |
| .091 | .10162 | .25032 | .15088 | .05856 | .44590 | .26877 | .10432 |
| .092 | .09970 | .25148 | .15305 | .05997 | .44573 | .27126 | .10629 |
| .093 | .09777 | .25260 | .15520 | .06140 | .44553 | .27374 | .10829 |
| .094 | .09582 | .25368 | .15735 | .06283 | .44529 | .27621 | .11030 |
| .095 | .09386 | .25472 | .15949 | .05429 | .44503 | .27866 | .11232 |
| .096 | .09189 | .25572 | .16163 | .06576 | .44473 | .28110 | .11436 |
| .097 | .08991 | .25668 | .15376 | .06724 | .44440 | .28352 | .11641 |
| .098 | .08792 | .25760 | .16588 | .06874 | .44404 | .28593 | .11848 |
| .099 | .08592 | .25849 | .16799 | .07025 | .44365 | .28832 | .12057 |
| .100 | .08391 | .25934 | .17009 | .07177 | .44323 | .29070 | .12266 |
| .101 | .08190 | .26016 | .17219 | .07331 | .44278 | .29306 | .12477 |
| .102 | .07987 | .26093 | .17427 | .07486 | .44230 | .29540 | .12690 |
| .103 | .07785 | .26168 | .17635 | .07643 | .44180 | .29773 | .12904 |
| .104 | .07581 | .26238 | .17841 | .07801 | .44127 | .30005 | .13119 |
| .105 | .07377 | .26306 | .18047 | .07960 | .44071 | .30234 | .13335 |
| .106 | .07173 | .26369 | .18251 | .08120 | .44012 | .30462 | .13553 |
| .107 | .06969 | .26430 | .18455 | .08282 | .43951 | .30689 | .13772 |
| .108 | .06764 | .26488 | .18657 | .08445 | .43887 | .30913 | .13993 |
| .109 | .06559 | .26540 | .18858 | .08609 | .43820 | .31136 | .14214 |
| .110 | .06353 | .26590 | .19058 | .08774 | .43751 | .31358 | .14437 |
| .111 | .06148 | .26637 | .19257 | .08941 | .43680 | .31577 | .14661 |
| .112 | .05943 | .26681 | .19454 | .09109 | .43606 | .31795 | .14886 |
| .113 | .05737 | .26722 | .19651 | .09277 | .43530 | .32011 | .15113 |
| .114 | .05532 | .26759 | .19846 | .09447 | .43452 | .32225 | .15341 |
| .115 | .05326 | .26794 | .20040 | .09618 | .43371 | .32438 | .15569 |
| .116 | .05121 | .26825 | .20232 | .09791 | .43288 | .32649 | .15799 |
| .117 | .04916 | .26854 | .20424 | .09964 | .43203 | .32858 | .16030 |
| .118 | .04712 | .26879 | .20613 | .10138 | .43116 | .33065 | .16262 |
| .119 | .04507 | .26902 | .20802 | .10314 | .43026 | .33270 | .16495 |
| .120 | .04303 | .26922 | .20989 | .10490 | .42935 | .33474 | .16729 |

TABLE 5C

| p | A* (1) | A* (2) | Ratio A* (2)/A*(1) |
|---|---|---|---|
| .000 | | | |
| .001 | .00143 | .00020 | .14282 |
| .002 | .00286 | .00041 | .14241 |
| .003 | .00429 | .00062 | .14401 |
| .004 | .00571 | .00083 | .14461 |
| .005 | .00714 | .00104 | .14521 |
| .006 | .00855 | .00125 | .14581 |
| .007 | .00997 | .00146 | .14641 |
| .008 | .01138 | .00167 | .14702 |
| .009 | .01279 | .00189 | .14762 |
| .010 | .01420 | .00210 | .14823 |
| .011 | .01560 | .00232 | .14884 |
| .012 | .01700 | .00254 | .14945 |
| .013 | .01840 | .00276 | .15006 |
| .014 | .01979 | .00298 | .15067 |
| .015 | .02119 | .00321 | .15128 |
| .016 | .02257 | .00343 | .15190 |
| .017 | .02396 | .00365 | .15251 |
| .018 | .02534 | .00388 | .15313 |
| .019 | .02672 | .00411 | .15375 |
| .020 | .02810 | .00434 | .15437 |
| .021 | .02947 | .00457 | .15499 |
| .022 | .03084 | .00480 | .15562 |
| .023 | .03221 | .00503 | .15624 |
| .024 | .03358 | .00527 | .15687 |
| .025 | .03494 | .00550 | .15749 |
| .026 | .03630 | .00574 | .15812 |
| .027 | .03766 | .00598 | .15875 |
| .028 | .03901 | .00622 | .15938 |
| .029 | .04036 | .00646 | .16002 |
| .030 | .04171 | .00670 | .16065 |
| .031 | .04305 | .00694 | .16129 |
| .032 | .04439 | .00719 | .16192 |
| .033 | .04573 | .00743 | .16256 |
| .034 | .04707 | .00768 | .16320 |
| .035 | .04840 | .00793 | .16384 |
| .036 | .04973 | .00818 | .16449 |
| .037 | .05106 | .00843 | .16513 |
| .038 | .05238 | .00868 | .16578 |
| .039 | .05370 | .00894 | .16642 |
| .040 | .05502 | .00919 | .16707 |
| .041 | .05633 | .00945 | .16772 |
| .042 | .05764 | .00971 | .16837 |
| .043 | .05895 | .00996 | .16903 |

TABLE 5C-continued

| p | A* (1) | A* (2) | Ratio A* (2)/A*(1) |
|---|--------|--------|--------------------|
| .044 | .06026 | .01022 | .16968 |
| .045 | .06156 | .01049 | .17034 |
| .046 | .06286 | .01075 | .17099 |
| .047 | .06416 | .01101 | .17165 |
| .048 | .06545 | .01128 | .17231 |
| .049 | .06675 | .01155 | .17297 |
| .050 | .06803 | .01181 | .17364 |
| .051 | 0.6932 | .01208 | .17430 |
| .052 | .07060 | .01235 | .17497 |
| .053 | .07188 | .01263 | .17564 |
| .054 | .07316 | .01290 | .17631 |
| .055 | .07443 | .01317 | .17698 |
| .056 | .07570 | .01345 | .17765 |
| .057 | .07697 | .01373 | .17833 |
| .058 | .07823 | .01400 | .17900 |
| .059 | .07950 | .01428 | .17968 |
| .060 | .08076 | .01456 | .18036 |
| .061 | .08201 | .01485 | .18104 |
| .062 | .08326 | .01513 | .18172 |
| .063 | .08451 | .01542 | .18240 |
| .064 | .08576 | .01570 | .18309 |
| .065 | .08701 | .01599 | .18378 |
| .066 | .08825 | .01628 | .18446 |
| .067 | .08949 | .01657 | .18515 |
| .068 | .09072 | .01686 | .18585 |
| .069 | .09195 | .01715 | .18654 |
| .070 | .09318 | .01745 | .18723 |
| .071 | .09441 | .01774 | .18793 |
| .072 | .09563 | .01804 | .18863 |
| .073 | .09685 | .01834 | .18933 |
| .074 | .09807 | .01865 | .19003 |
| .075 | .09929 | .01894 | .19073 |
| .076 | .10050 | .01924 | .19144 |
| .077 | .10171 | .01954 | .19214 |
| .078 | .10291 | .01985 | .19285 |
| .079 | .10412 | .02015 | .19356 |
| .080 | .10532 | .02046 | .19427 |
| .081 | .10651 | .02077 | .19499 |
| .082 | .10771 | .02108 | .19570 |
| .083 | .10890 | .02139 | .19642 |
| .084 | .11009 | .02170 | .19714 |
| .085 | .11127 | .02202 | .19786 |
| .086 | .11245 | .02233 | .19858 |
| .087 | .11363 | .02265 | .19930 |
| .088 | .11481 | .02296 | .20003 |
| .089 | .11598 | .02328 | .20075 |
| .090 | .11715 | .02360 | .20148 |
| .091 | .11832 | .02393 | .20221 |
| .092 | .11949 | .02425 | .20294 |
| .093 | .12065 | .02457 | .20368 |
| .094 | .12181 | .02490 | .20441 |
| .095 | .12296 | .02523 | .20515 |
| .096 | .12412 | .02555 | .20589 |
| .097 | .12527 | .02588 | .20663 |
| .098 | .12641 | .02621 | .20737 |
| .099 | .12756 | .02655 | .20812 |
| .100 | .12870 | .02688 | .20886 |
| .101 | .12984 | .02722 | .20961 |
| .102 | .13097 | .02755 | .21036 |
| .103 | .13210 | .02789 | .21111 |
| .104 | .13323 | .02823 | .21187 |
| .105 | .13436 | .02857 | .21262 |
| .106 | .13548 | .02891 | .21338 |
| .107 | .13660 | .02925 | .21414 |
| .108 | .13772 | .02960 | .21490 |
| .109 | .13884 | .02994 | .21566 |
| .110 | .13955 | .03029 | .21643 |
| .111 | .14106 | .03064 | .21719 |
| .112 | .14216 | .03099 | .21796 |
| .113 | .14327 | .03134 | .21873 |
| .114 | .14437 | .03169 | .21950 |
| .115 | .14546 | .03204 | .22028 |
| .116 | .14656 | .03240 | .22105 |
| .117 | .14765 | .03275 | .22183 |
| .118 | .14874 | .03311 | .22261 |
| .119 | .14982 | .03347 | .22339 |
| .120 | .15090 | .03383 | .22418 |
| .121 | .15198 | .03419 | .22496 |
| .122 | .15306 | .03455 | .22575 |
| .123 | .15413 | .03492 | .22654 |
| .124 | .15521 | .03528 | .22733 |
| .125 | .15627 | .03565 | .22813 |
| .126 | .15734 | .03602 | .22892 |
| .127 | .15840 | .03639 | .22972 |
| .128 | .15946 | .03676 | .23052 |
| .129 | .16051 | .03713 | .23132 |
| .130 | .16157 | .03750 | .23212 |
| .131 | .16282 | .03788 | .23293 |
| .132 | .16366 | .03825 | .23374 |
| .133 | .16471 | .03863 | .23455 |
| .134 | .16575 | .03901 | .23536 |
| .135 | .16679 | .03939 | .23617 |
| .136 | .16782 | .03977 | .23699 |
| .137 | .16886 | .04015 | .23781 |
| .138 | .16989 | .04054 | .23863 |
| .139 | .17091 | .04092 | .23945 |
| .140 | .17194 | .04131 | .24027 |
| .141 | .17296 | .04170 | .24110 |
| .142 | .17397 | .04209 | .24193 |
| .143 | .17499 | .04248 | .24276 |
| .144 | .17600 | .04287 | .24359 |
| .145 | .17701 | .04327 | .24442 |
| .146 | .17801 | .04366 | .24526 |
| .147 | .17902 | .04406 | .24610 |
| .148 | .18002 | .04445 | .24694 |
| .149 | .18102 | .04485 | .24779 |
| .150 | .18201 | .04525 | .24863 |
| .151 | .18300 | .04565 | .25948 |
| .152 | .18399 | .04606 | .25033 |
| .153 | .18497 | .04646 | .25118 |
| .154 | .18596 | .04687 | .25203 |
| .155 | .18694 | .04727 | .25289 |
| .156 | .18791 | .04768 | .25375 |
| .157 | .18889 | .04809 | .25461 |
| .158 | .18986 | .04850 | .25547 |
| .159 | .19082 | .04892 | .25634 |
| .160 | .19179 | .04933 | .25721 |
| .161 | .19275 | .04974 | .25808 |
| .162 | .19371 | .05016 | .25895 |
| .163 | .19467 | .05058 | .25982 |
| .164 | .19562 | .05100 | .26070 |
| .165 | .19657 | .05142 | .26158 |
| .166 | .19752 | .05184 | .25246 |
| .167 | .19846 | .05226 | .26335 |
| .168 | .19940 | .05269 | .26423 |
| .169 | .20034 | .05311 | .26512 |
| .170 | .20127 | .05354 | .26601 |
| .171 | .20221 | .05397 | .26691 |
| .172 | .20314 | .05440 | .26780 |
| .173 | .20406 | .05483 | .26870 |
| .174 | .20499 | .05526 | .26960 |
| .175 | .20591 | .05570 | .27050 |
| .176 | .20682 | .05613 | .27141 |
| .177 | .20774 | .05657 | .27231 |
| .178 | .20865 | .05701 | .27322 |
| .179 | .20956 | .05745 | .27414 |
| .180 | .21047 | .05789 | .27505 |
| .181 | .21137 | .05833 | .27597 |
| .182 | .21227 | .05877 | .27689 |
| .183 | .21316 | .05922 | .27781 |
| .184 | .21406 | .05967 | .27874 |
| .185 | .21495 | .06011 | .27966 |
| .186 | .21584 | .06056 | .28059 |
| .187 | .21672 | .06101 | .28153 |
| .188 | .21761 | .06147 | .28246 |
| .189 | .21848 | .06192 | .28340 |
| .190 | .29136 | .06237 | .28434 |
| .191 | .22023 | .06283 | .28528 |
| .192 | .22110 | .06329 | .28623 |
| .193 | .22197 | .06374 | .28717 |
| .194 | .22284 | .06420 | .28812 |
| .195 | .22370 | .06467 | .28908 |
| .196 | .22456 | .06513 | .29003 |
| .197 | .22541 | .06559 | .29099 |
| .198 | .22627 | .06606 | .29195 |
| .199 | .22712 | .06653 | .29291 |
| .200 | .22796 | .06699 | .29388 |

It is claimed:

1. A method for determining the proportion of mass isotopically labeled subunits in a subunit precursor pool from which a biopolymer containing at least two such subunits is synthesized in a subject, comprising administering to the subject, a mass isotopically labeled precursor subunit:

by said administering, producing after a selected period of subunit incorporation, an enrichment of the mass isotopically labeled subunit in the biopolymer;

isolating the biopolyme recomprising at least two subunits from the subject after said incorporation period;

determining relative frequencies of at least two different mass isotopomers of the biopolymer using mass spectrometer wherein each said mass isotopomer comprises at least two biopoymer subunits and wherein each said mass isotopomer contains at least one mass isotopically labeled subunit; and calculating from said relative frequencies, the proportion of mass isotopically labeled subunits in the subunit precursor pool from which the biopolymer was synthesized.

2. The method of claim 1, wherein said calculating includes comparing the relative frequencies of said different mass isotopomers of the biopolymer with statistically expected frequencies of mass isotopically labeled subunits in a biopolymer formed from a pool containing different ratios of unlabeled and mass isotopically labeled subunits.

3. The method of claim 1, wherein said determining includes correcting the relative frequencies of said different mass isotopomers of the biopolymer for the relative frequencies of such biopolymers prior to said administering.

4. The method of claim 3, wherein said correcting includes measuring the relative frequencies of said different mass isotopomers of the biopolymer before said administering, and subtracting these frequencies from the frequencies determined after said selected period of incorporation.

5. A method for measuring the rate of synthesis of a biopolymer which is formed from a subunit contained in a precursor subunit pool in a subject, comprising administering to the subject, a mass isotopically labeled precursor subunit;

by said administering, producing after a selected period of subunit incorporation, an enrichment of the mass isotopically labeled subunit in the biopolymer;

isolating the biopolymer comprising at least two subunits from the subject after said incorporation period;

determining relative frequencies of at least two different mass isotopomers of the biopolymer using mass spectrometry wherein said mass isotopomer comprises at least two biopolymer subunits, and wherein each said mass isotopomer contains at least one mass isotopically labeled subunit;

calculating from said relative frequencies, the proportion of mass isotopically labeled subunits in the subunit pool from which the biopolymer was synthesized;

from said calculated proportion of mass isotopically labeled subunit present in the precursor subunit pool, calculating an expected frequency of mass isotopomers of a biopolymer sunthesized from said precursor subunit pool and containing at least one mass isotopically labeled subunit; and comparing said expected frequency of said biopolymer with the actual determined frequency, to determine the proportion of biopolymer which is synthesized during said selected incorporation period.

6. The method of claim 5, wherein said calculating includes comparing the relative frequencies of said different mass isotopomers of the biopolymer with statistically expected frequencies of mass isotopically labeled subunits in a biopolymer formed from a pool containing different ratios of unlabeled and mass isotopically labeled subunits.

7. The method of claim 5, wherein said determining includes correcting the relative frequencies of said different mass isotopomers of the biopolymer for the relative frequencies of such biopolymers prior to said administering.

8. The method of claim 7, wherein said correcting includes measuring the relative frequencies of said different mass isotopomers of the biopolymer before said administering, and subtracting these frequencies from the frequencies determined after said selected period of incorporation.

9. A method for measuring the rate of in vivo decay of an isotopically labeled biopolymer which is formed from a subunit contained in a precursor subunit pool in a subject, comprising administering to the subject, a mass isotopically labeled precursor subunit;

by said administering, producing after a selected period of subunit incorporation, a mass isotopomer of a biopolymer comprising at least two subunits which mass isotopomer is produced in negligible amounts only prior to said administering;

isolating the biopolymer from the subject at least two different times after said administering;

determining frequencies of said mass isotopomer of the biopolymer using mass spectrometry wherein said biopolymer comprises at least two subunits, at said different times; and from said determined frequencies, calculating the rate of decay of the isotopically labeled biopolymer.

* * * * *